(12) United States Patent
Yoshida et al.

(10) Patent No.: US 10,023,578 B2
(45) Date of Patent: Jul. 17, 2018

(54) CRYSTALS OF DISPIROPYRROLIDINE DERIVATIVES

(71) Applicant: Daiichi Sankyo Company, Limited, Tokyo (JP)

(72) Inventors: Shoko Yoshida, Tokyo (JP); Yuuichi Sugimoto, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 15/887,444

(22) Filed: Feb. 2, 2018

(65) Prior Publication Data

US 2018/0155355 A1 Jun. 7, 2018

Related U.S. Application Data

(60) Division of application No. 15/370,160, filed on Dec. 6, 2016, now Pat. No. 9,884,871, which is a continuation of application No. 15/144,485, filed on May 2, 2016, now Pat. No. 9,540,386, which is a division of application No. 14/426,630, filed as application No. PCT/JP2013/073865 on Sep. 5, 2013, now Pat. No. 9,359,368.

(30) Foreign Application Priority Data

Sep. 6, 2012 (JP) .................. 2012-195761

(51) Int. Cl.
   *C07D 487/10* (2006.01)
   *A61K 31/4439* (2006.01)

(52) U.S. Cl.
   CPC ........ *C07D 487/10* (2013.01); *A61K 31/4439* (2013.01); *C07B 2200/13* (2013.01)

(58) Field of Classification Search
   CPC .................................................. C07D 487/10
   USPC ............................................ 514/278; 546/15
   See application file for complete search history.

(56) References Cited

U.S. PATENT DOCUMENTS

| 8,629,133 | B2 * | 1/2014 | Sugimoto ............ C07D 487/10 514/210.21 |
|---|---|---|---|
| 9,359,368 | B2 | 6/2016 | Yoshida et al. |
| 9,540,386 | B2 | 1/2017 | Yoshida et al. |
| 9,718,830 | B2 | 8/2017 | Yoshida et al. |
| 9,718,831 | B2 | 8/2017 | Yoshida et al. |
| 9,745,315 | B2 | 8/2017 | Yoshida et al. |
| 9,884,871 | B2 | 2/2018 | Yoshida et al. |
| 2011/0301176 | A1 | 12/2011 | Uoto et al. |
| 2012/0289494 | A1 | 11/2012 | Wang et al. |

FOREIGN PATENT DOCUMENTS

| CN | 103635473 A | 3/2014 |
|---|---|---|
| WO | WO 2006/024837 A1 | 3/2006 |
| WO | WO 2006/091646 A2 | 8/2006 |
| WO | WO 2006/136606 A2 | 12/2006 |
| WO | WO 2007/104664 A1 | 9/2007 |
| WO | WO 2007/104714 A1 | 9/2007 |
| WO | WO 2008/034736 A2 | 3/2008 |
| WO | WO 2008/036168 A2 | 3/2008 |
| WO | WO 2008/055812 A1 | 5/2008 |
| WO | WO 2008/119741 A2 | 10/2008 |
| WO | WO 2008/141917 A1 | 11/2008 |
| WO | WO 2008/141975 A1 | 11/2008 |
| WO | WO 2009/077357 A1 | 6/2009 |
| WO | WO 2009/080488 A1 | 7/2009 |
| WO | WO 2009/115425 A1 | 9/2009 |
| WO | WO 2010/028862 A1 | 3/2010 |
| WO | WO 2010/031713 A1 | 3/2010 |
| WO | WO 2010/082612 A1 | 7/2010 |
| WO | WO 2010/084097 A1 | 7/2010 |
| WO | WO 2010/091979 A1 | 8/2010 |
| WO | WO 2010/094622 A1 | 8/2010 |
| WO | WO 2010/121995 A1 | 10/2010 |
| WO | WO 2011/045257 A1 | 4/2011 |
| WO | WO 2011/060049 A2 | 5/2011 |
| WO | WO 2011/061139 A1 | 5/2011 |
| WO | WO 2011/067185 A1 | 6/2011 |
| WO | WO 2011/098398 A1 | 8/2011 |
| WO | WO 2011/101297 A1 | 8/2011 |
| WO | WO 2011/127058 A2 | 10/2011 |
| WO | WO 2011/134925 A1 | 11/2011 |
| WO | WO 2012/007409 A1 | 1/2012 |
| WO | WO 2012/022707 A1 | 2/2012 |
| WO | WO 2012/032466 A1 | 3/2012 |
| WO | WO 2012/034954 A1 | 3/2012 |
| WO | WO 2012/038307 A1 | 3/2012 |
| WO | WO 2012/076513 A1 | 6/2012 |
| WO | WO 2012/121361 A1 | 9/2012 |
| WO | WO 2012/155066 A2 | 11/2012 |

OTHER PUBLICATIONS

Bernstein, "Polymorphism in Molecular Crystals," Clarendon Press, Oxford, (2002), pp. 115-118 and 272.

Braga et al., "Making crystals from crystals: a green route to crystal engineering and polymorphism," *Chem. Commun.*, (2005), pp. 3635-3645.

Davidovich et al., "Detection of Polymorphism by Powder X-Ray Diffraction: Interference by Preferred Orientation," *Am. Pharm. Rev.*, (2004), 2(1):10, 12, 14, 16, 100.

Dean, "Analytical Chemistry Handbook," McGraw-Hill, Inc., New York, (1995), pp. 10.24-10.26.

Ding et al., "Structure-Based Design of Potent Non-Peptide MDM2 Inhibitors," *J. Am. Chem. Soc.*, (2005), 127:10130-10131.

Ding et al., "Structure-Based Design of Spiro-oxindoles as Potent, Specific Small-Molecule Inhibitors of the MDM2-p53 Interaction," *J. Med. Chem.*, (2006), 49:3432-3435.

(Continued)

*Primary Examiner* — Patricia L Morris
(74) *Attorney, Agent, or Firm* — Dorsey & Whitney LLP

(57) ABSTRACT

Crystals of a dispiropyrrolidine compound or a salt thereof which inhibits the action of Mdm2 are provided. The present invention provides crystals of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a salt thereof which inhibits Mdm2 and has anti-tumor activity. The present invention also provides a medicament comprising the same.

3 Claims, 12 Drawing Sheets

(56) References Cited

OTHER PUBLICATIONS

Ding et al., "Synthesis of spirooxindoles via asymmetric 1,3-dipolar cycloaddition," *Tetrahedron Letters*, (2005), 46:5949-5951.
Guillory (H.G. Brittain, Ed.), "Polymorphism in Pharmaceutical Solids," New York, Marcel Dekker, Inc., (1999), pp. 183-226.
Hardcastle et al., "Small-Molecule Inhibitors of the MDM2-p53 Protein-Protein Interaction Based on an Isoindolinone Scaffold," *J. Med. Chem.*, (2006), 49:6209-6221.
Ivanisevic et al., "Uses of X-Ray Powder Diffraction in the Pharmaceutical Industry," *Pharmaceutical Sciences Encyclopedia: Drug Discovery, Development, and Manufacturing*, (S.C. Gad, Ed.), John Wiley & Sons, Inc., (2010), pp. 1-42.
Kirk-Othmer, "Crystallization," *Kirk-Othmer Encyclopedia of Chemical Technology*, John Wiley & Sons, (2002), 8:95-147.
Pellegrini et al., "15. Total Synthesis of (+)-Elacomine and (−)-Isoelacomine, Two Hitherto Unnamed Oxindole Alkaloids from *Elaeagnus commutata*," *Helvetica Chimica Acta*, (1996), 79:151-168.
Rodriquez-Spong et al., "General principles of pharmaceutical solid polymorphism: a supramolecular perspective," *Advanced Drug Delivery Reviews*, (2004), 56:241-274.
Seddon, "Pseudopolymorph: A Polemic," *Crystal Growth and Design*, (2004), 4(6):1087, 2 pages from internet http://pubs.acs.org/cgi-bin/sample.cgi/cgdefu/2004/4/106/html/eg030084y.html.
Vippagunta et al., "Crystalline Solids," *Advanced Drug Delivery Reviews*, (2001), 48:3-26.
Yu et al., "Potent and Orally Active Small-Molecule Inhibitors of the MDM2-p53 Interaction," *J. Med. Chem.*, (2009), 52:7970-7973.
English translation of International Search Report dated Dec. 3, 2013, in PCT Application No. PCT/JP2013/073865, 2 pages.
English translation of Written Opinion dated Dec. 3, 2013, in PCT Application No. PCT/JP2013/073865, 5 pages.
English translation of International Preliminary Report on Patentability dated Mar. 10, 2015, in PCT Application No. PCT/JP2013/073865, 6 pages.

* cited by examiner

[Figure 1]
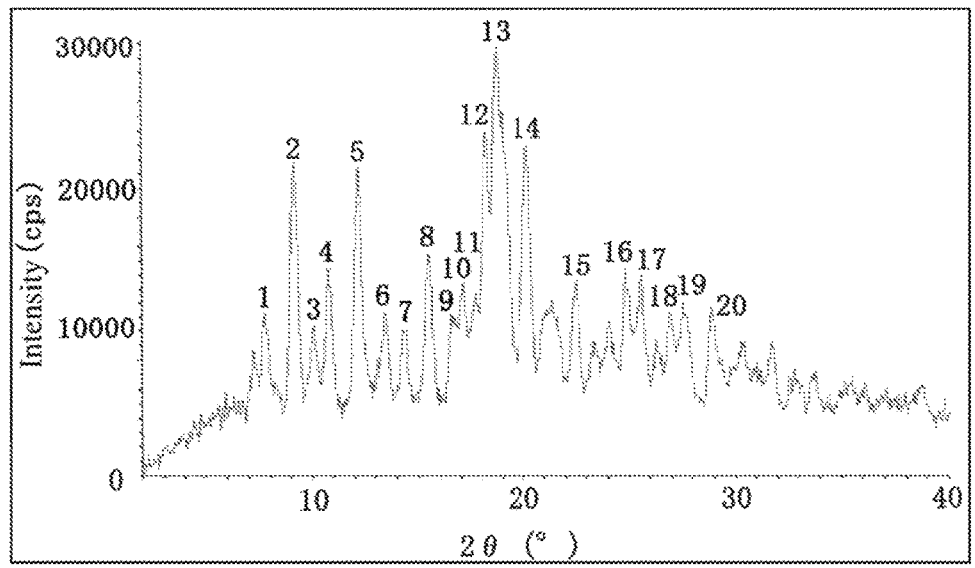
[Figure 2]
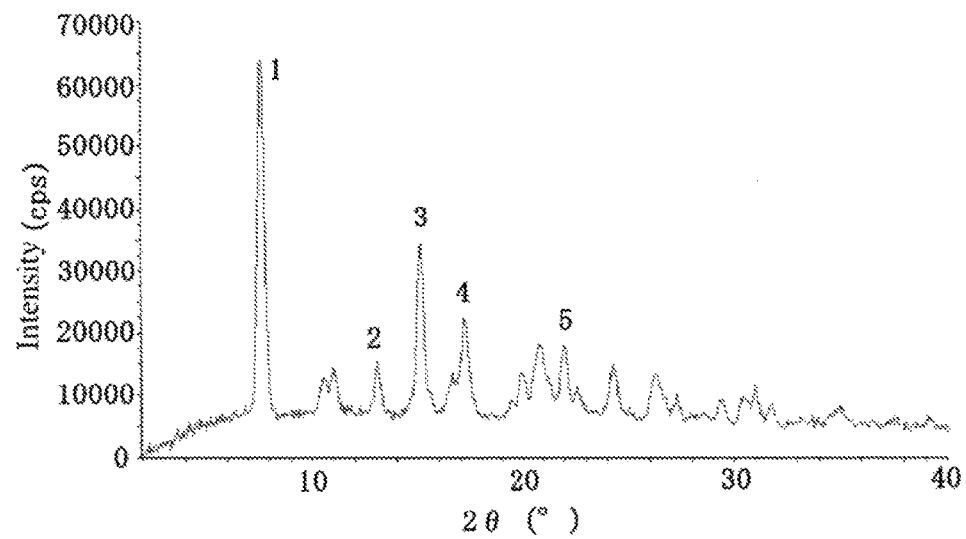

[Figure 3]
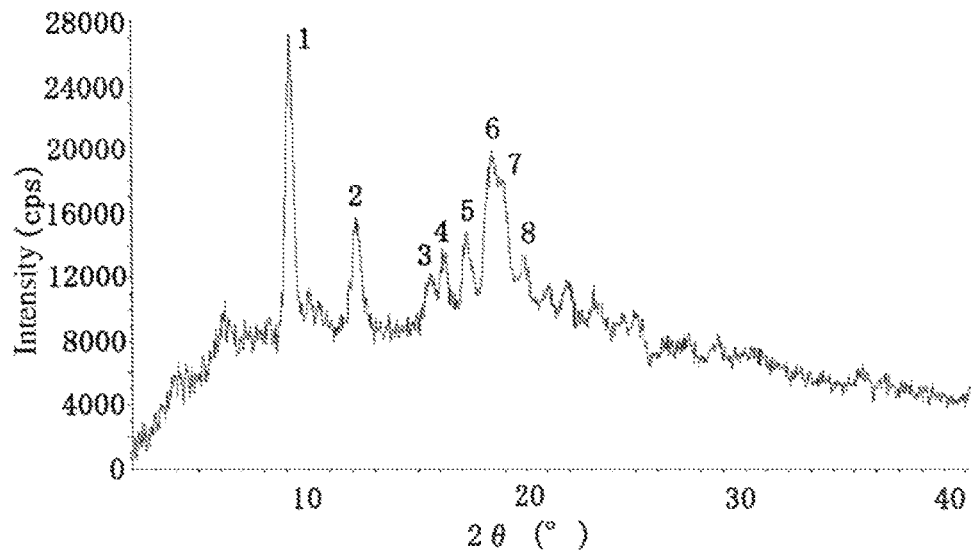
[Figure 4]
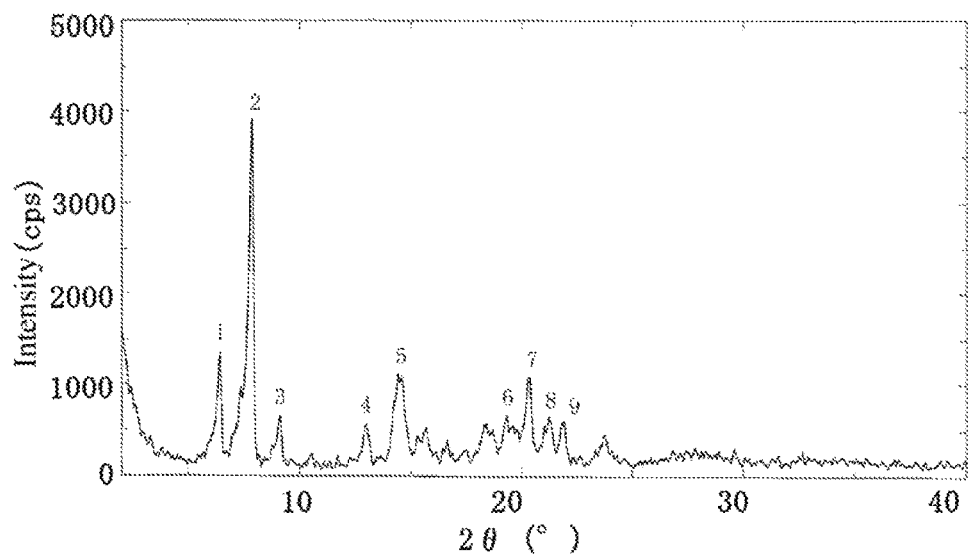

[Figure 5]
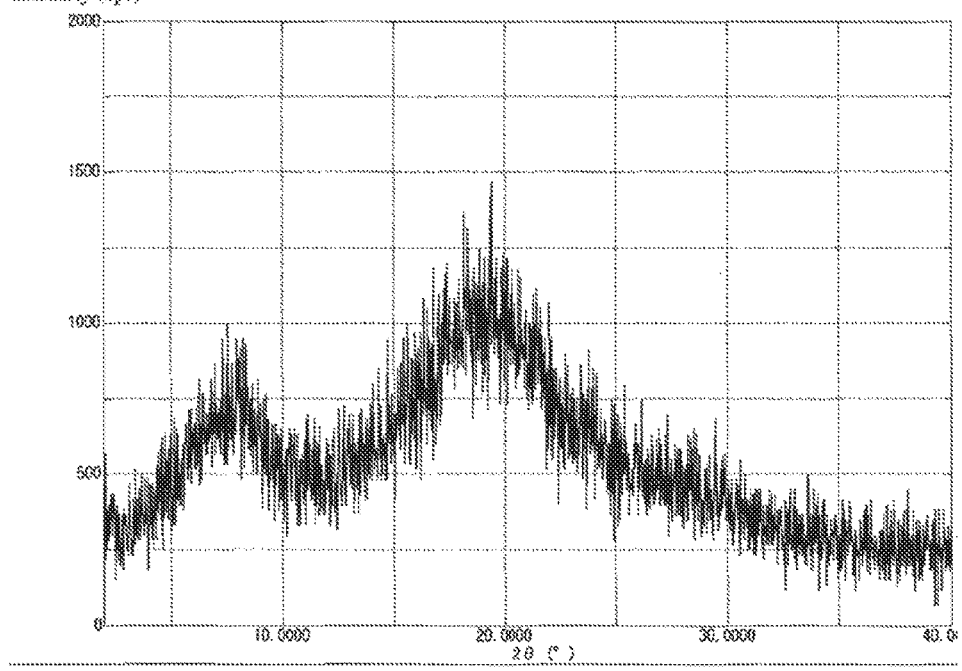
[Figure 6]
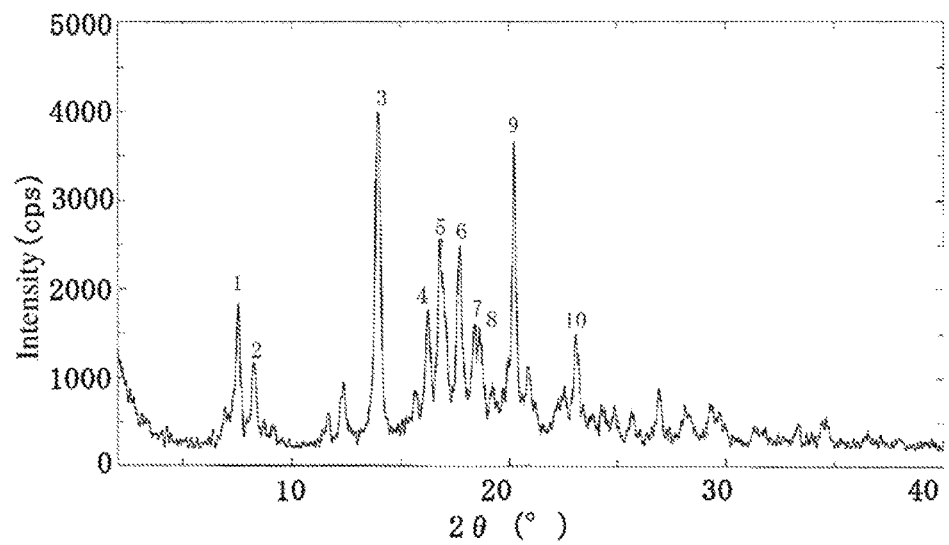

[Figure 7]
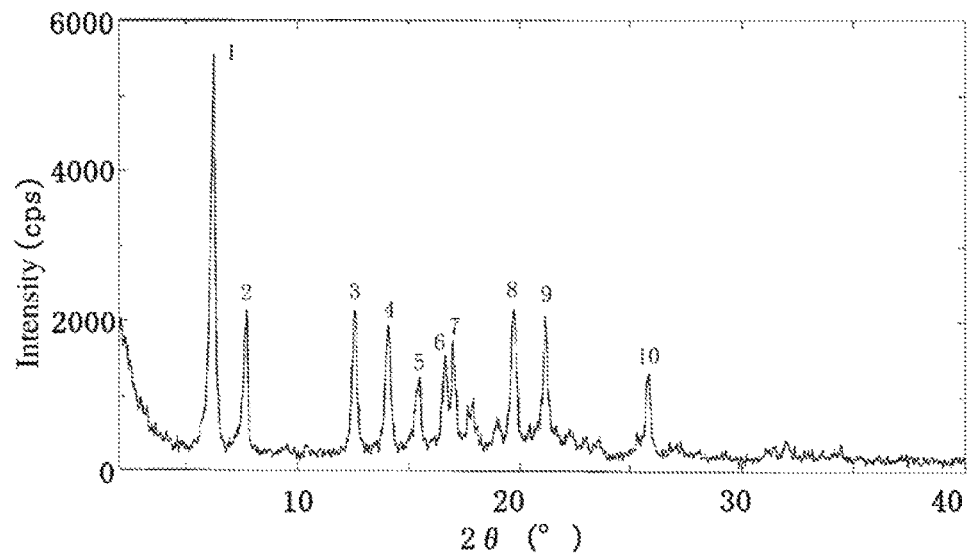
[Figure 8]
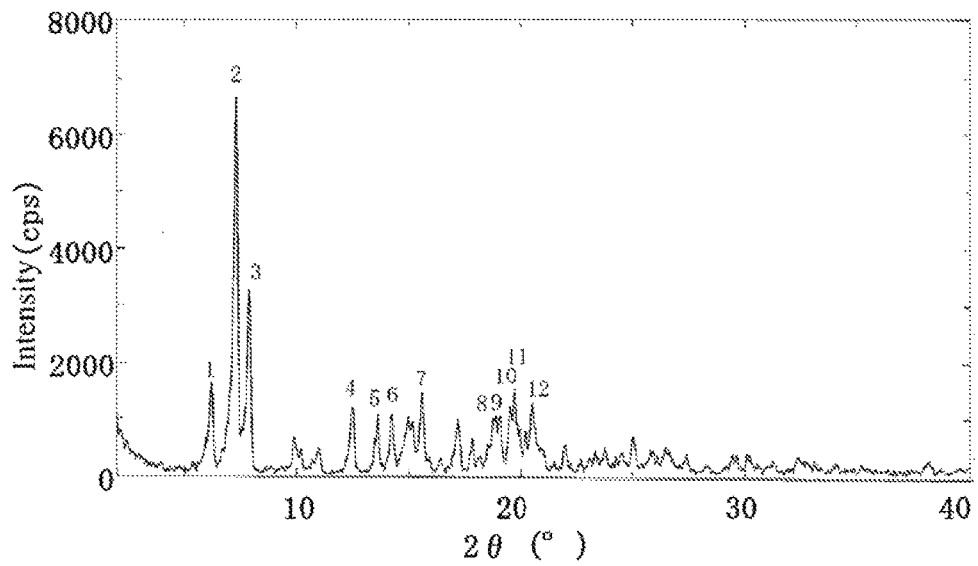

[Figure 9]
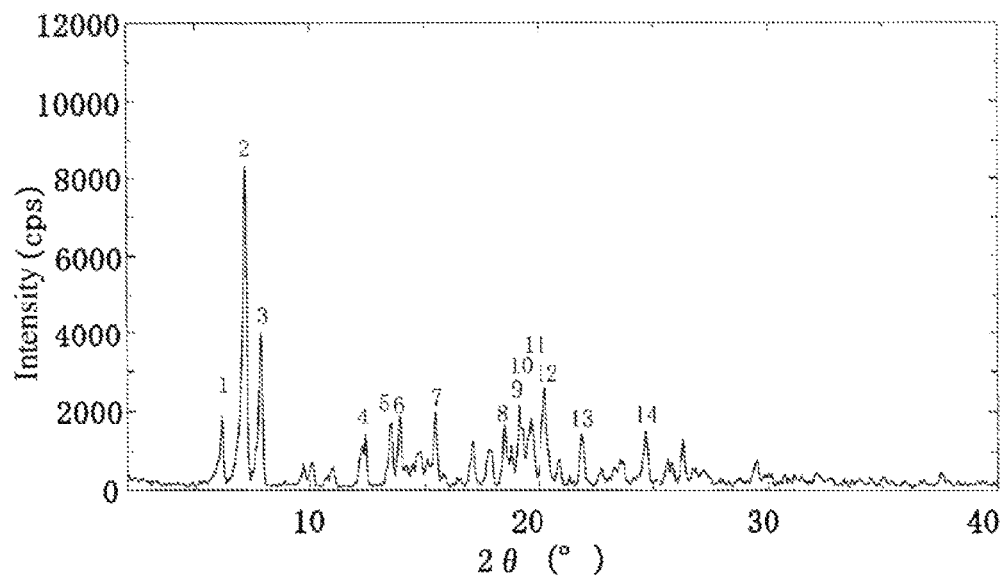
[Figure 10]
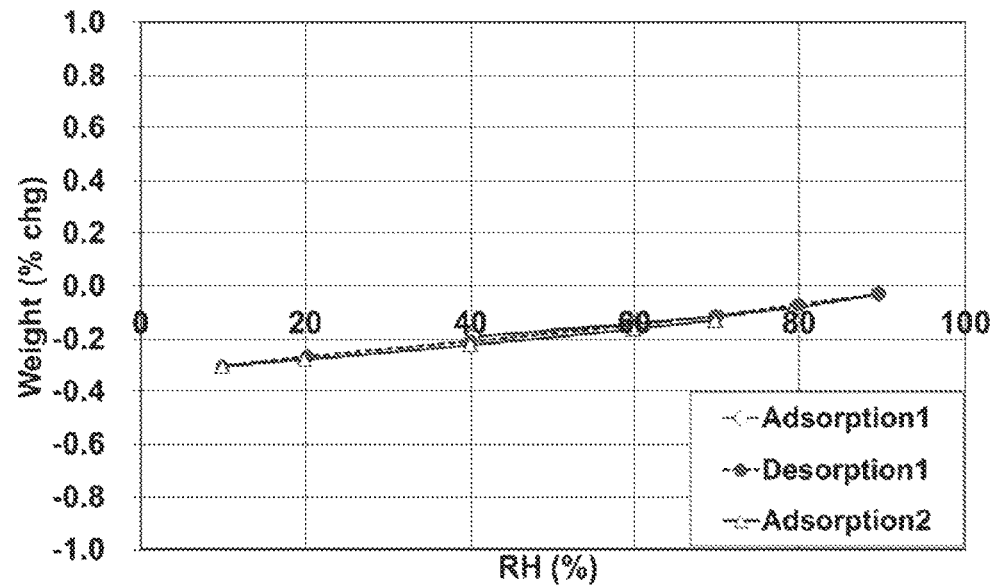

[Figure 11]
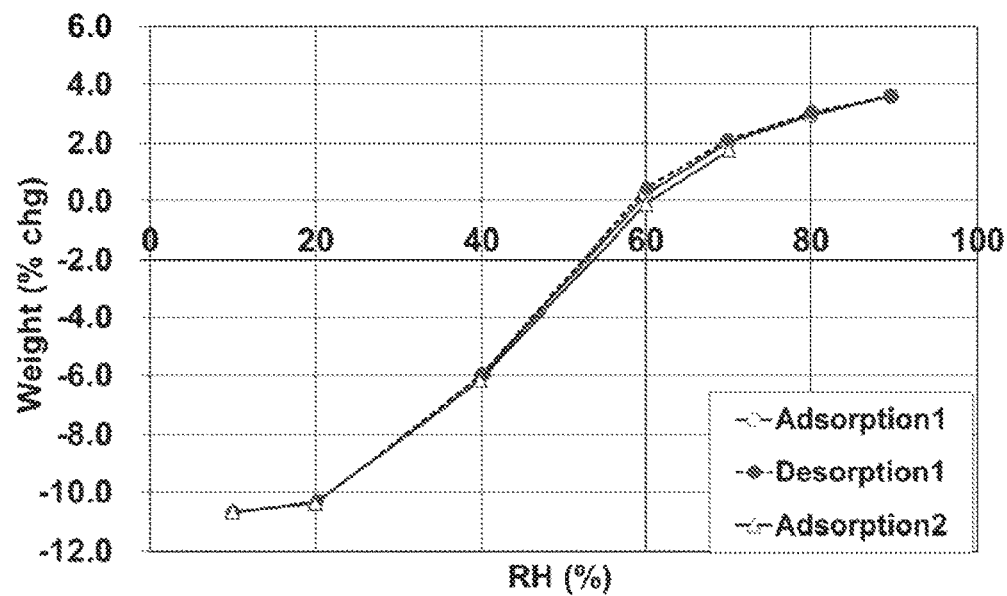
[Figure 12]
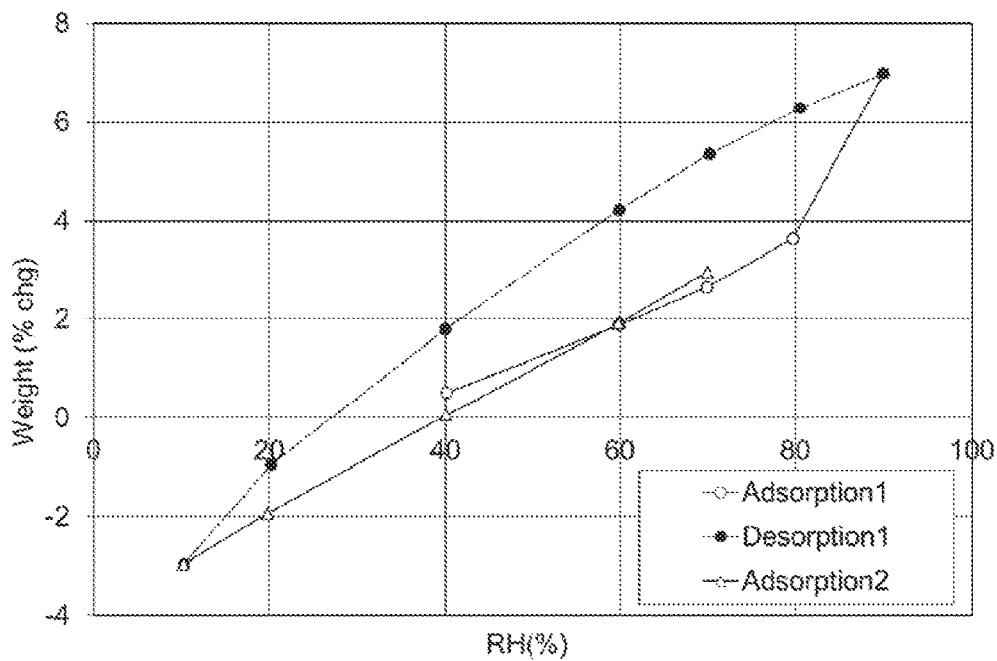

[Figure 13]
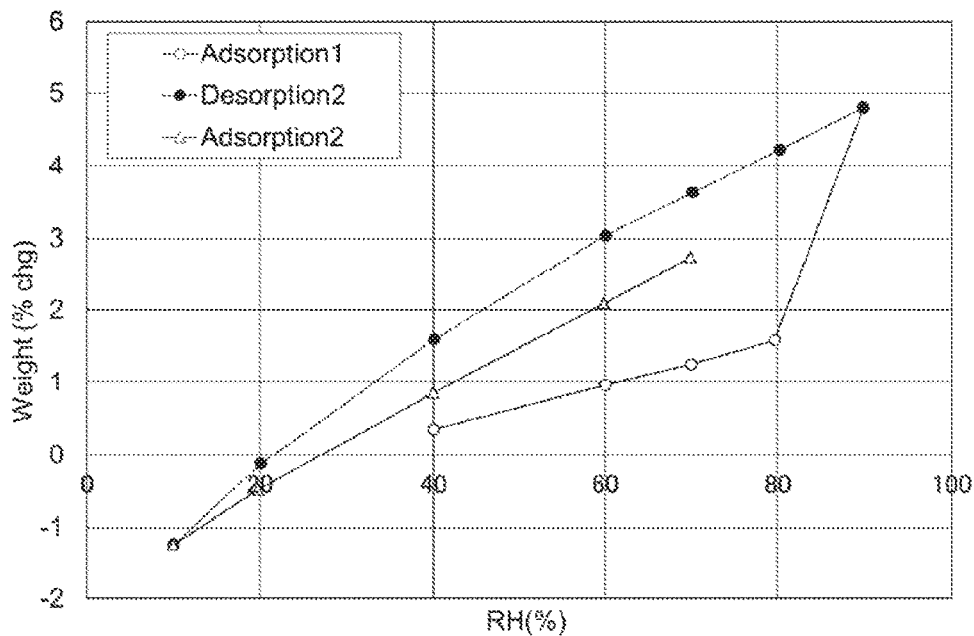
[Figure 14]
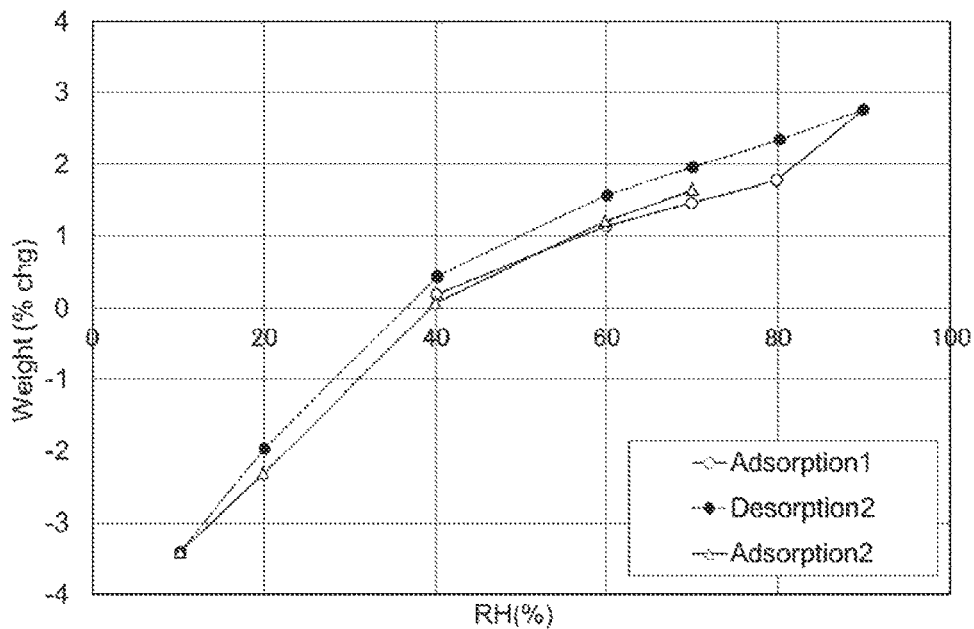

[Figure 15]
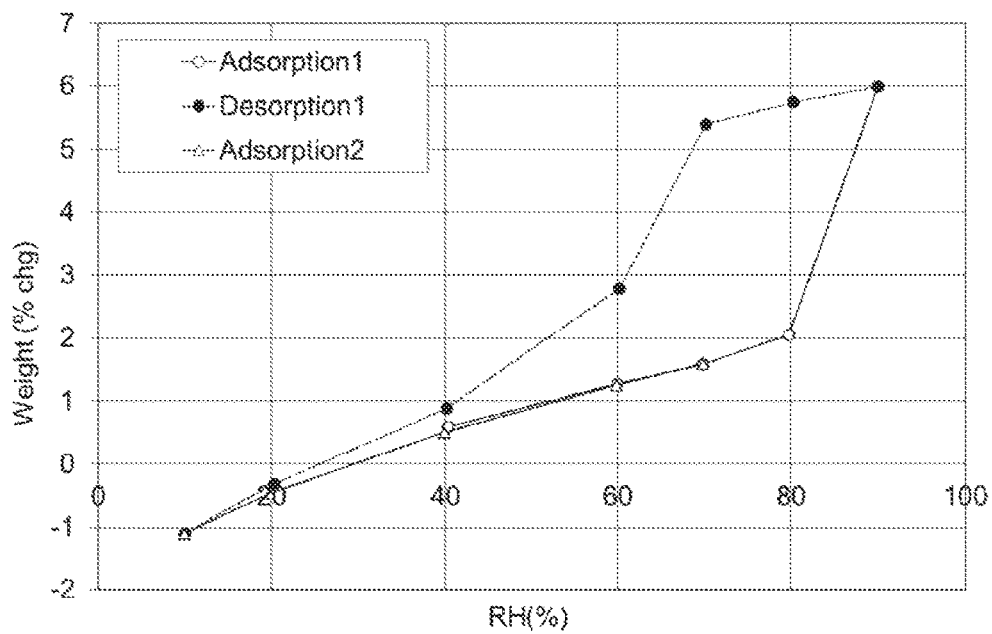
[Figure 16]
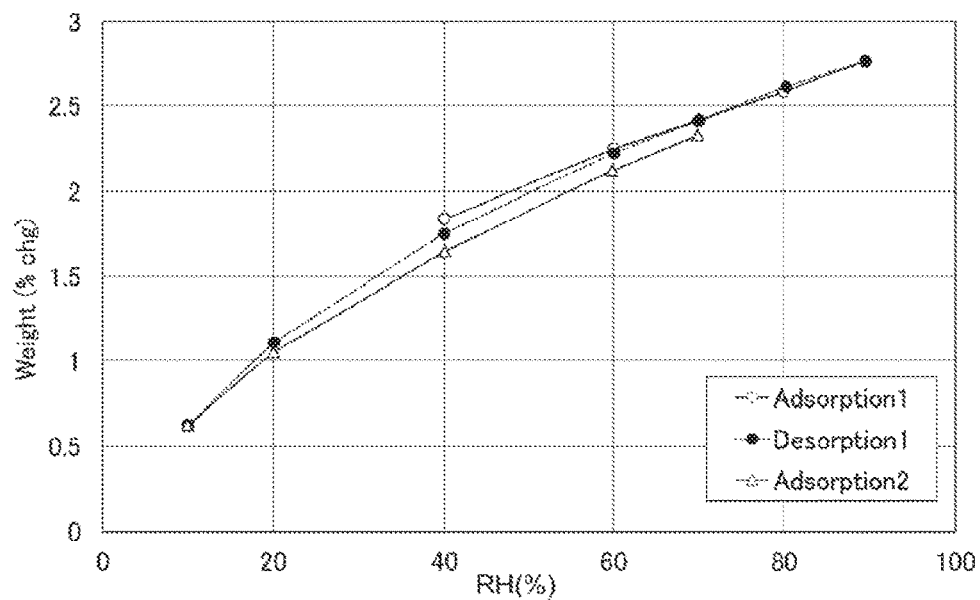

[Figure 17]
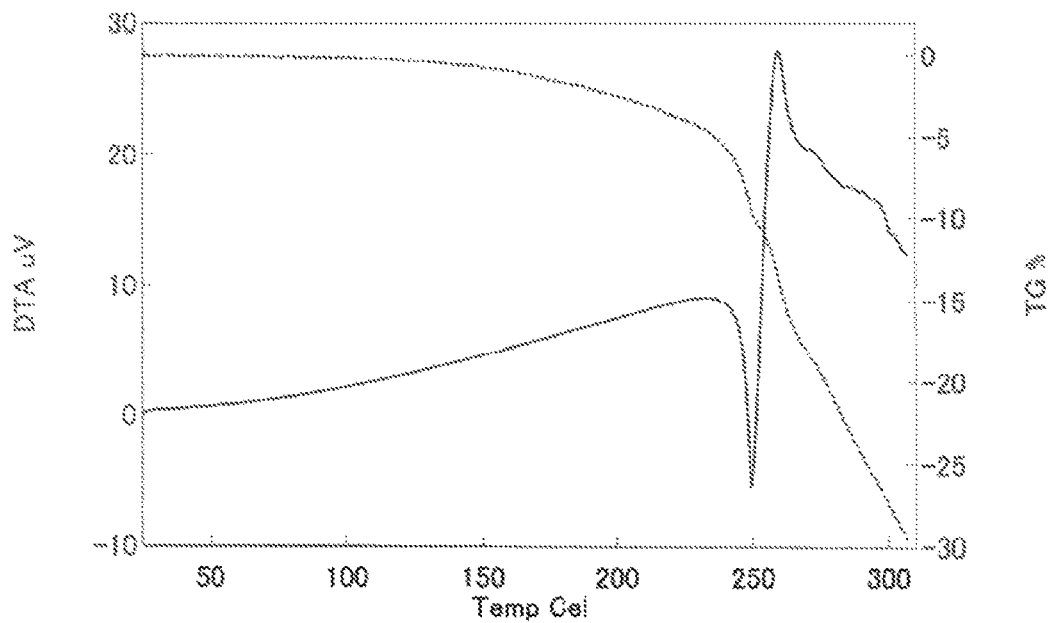
[Figure 18]
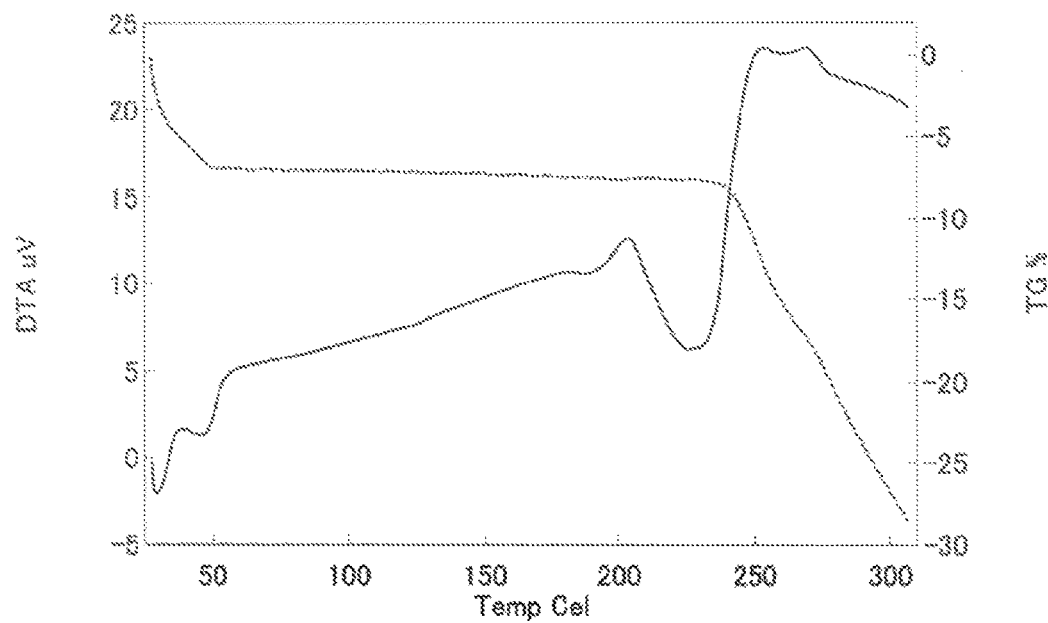

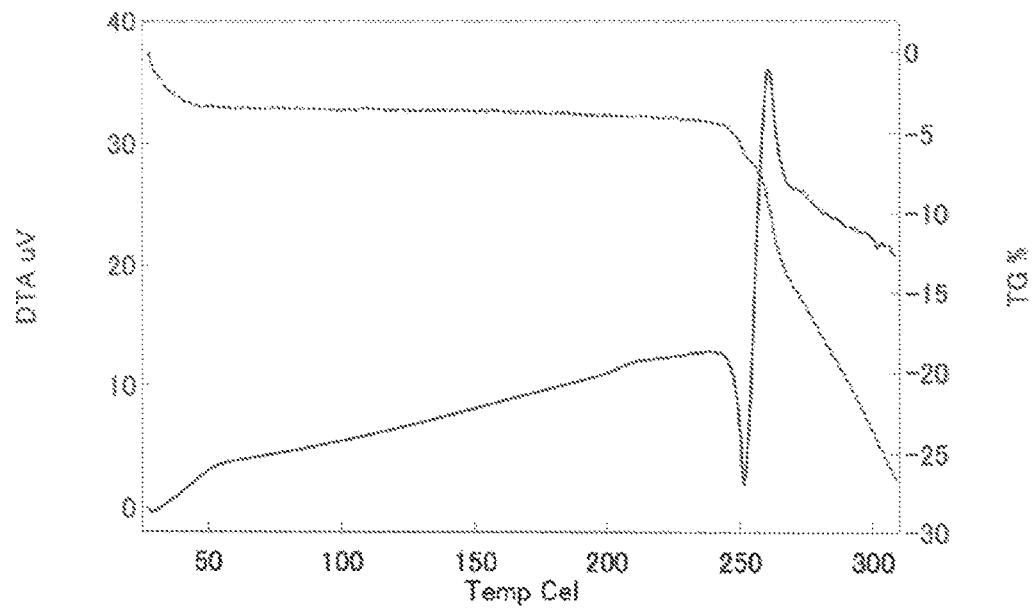
[Figure 19]
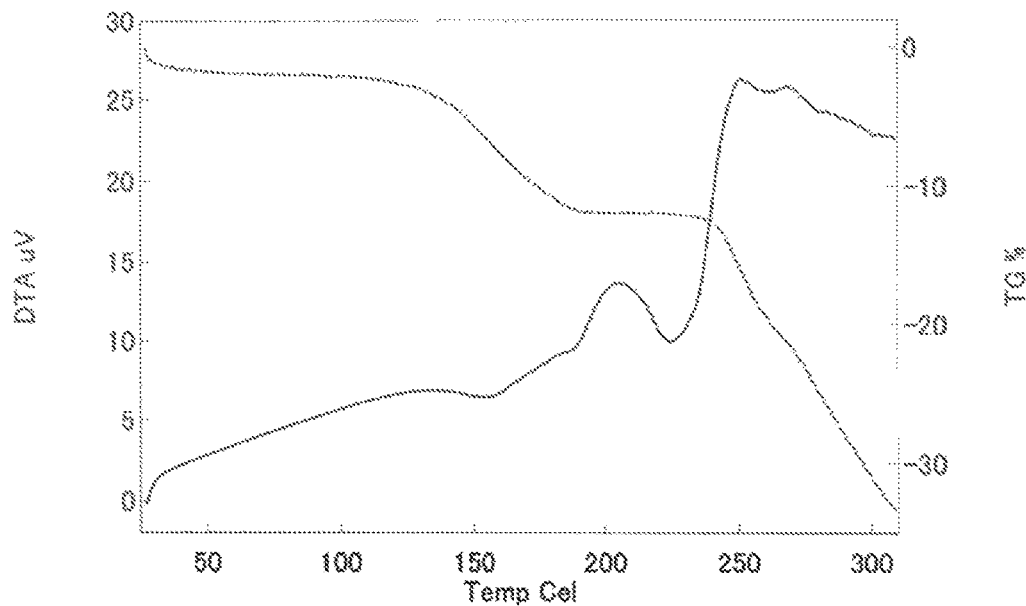
[Figure 20]

[Figure 21]
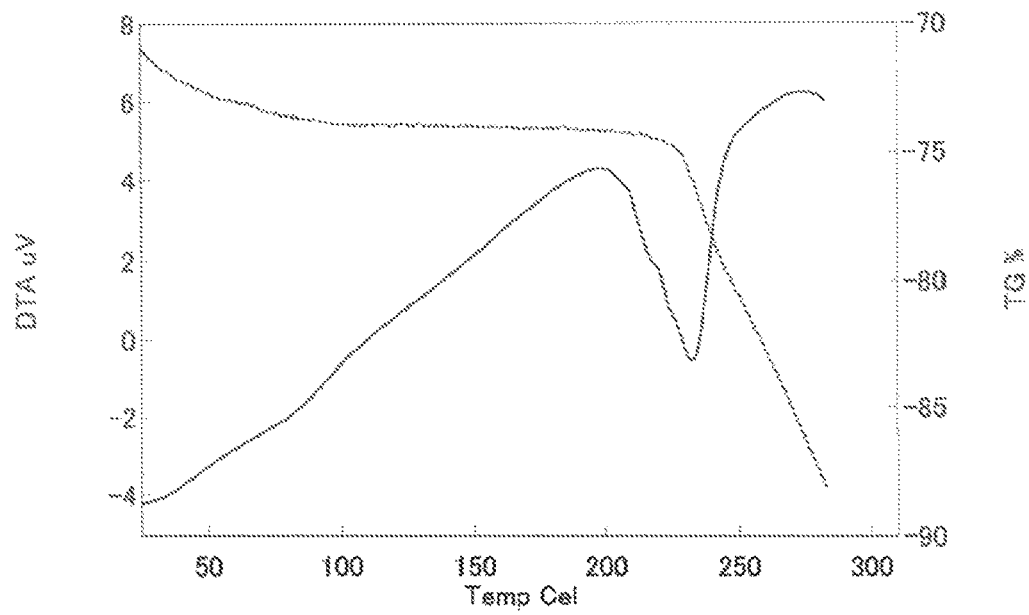
[Figure 22]
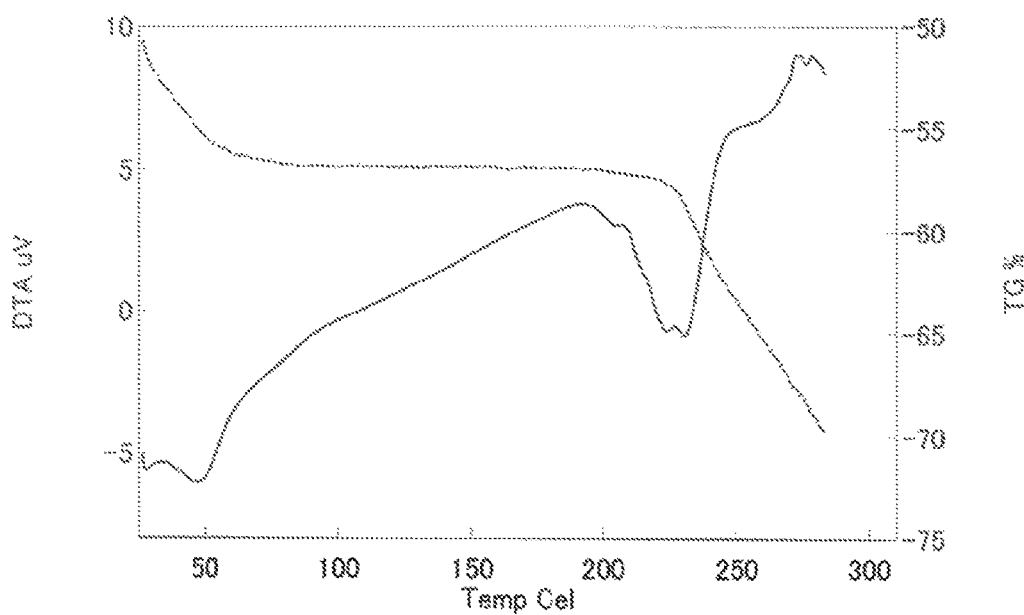

[Figure 23]
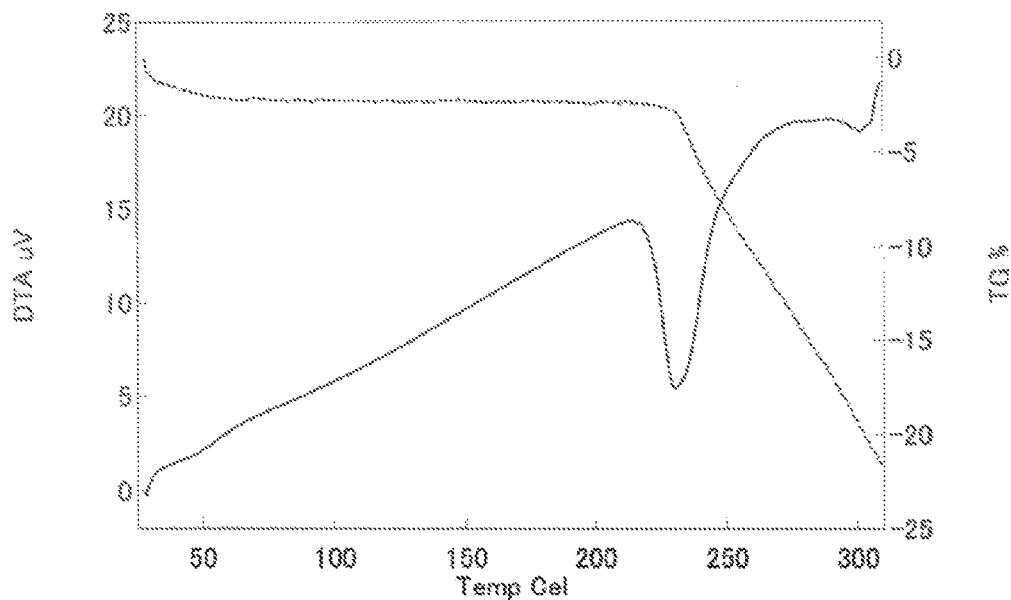
[Figure 24]
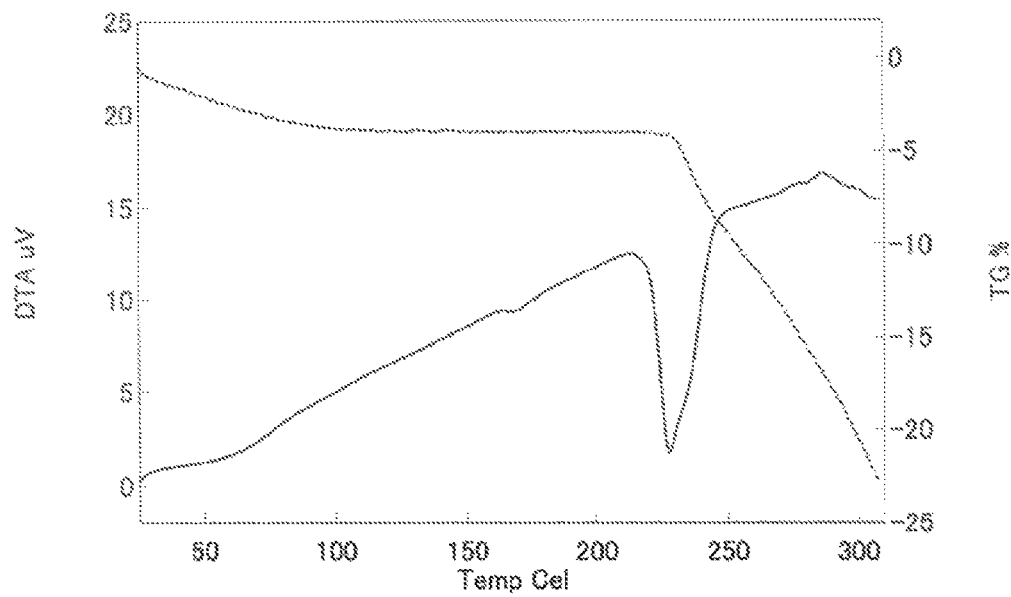

CRYSTALS OF DISPIROPYRROLIDINE DERIVATIVES

CROSS-REFERENCE TO RELATED APPLICATIONS

This application is a divisional application of U.S. patent application Ser. No. 15/370,160, filed Dec. 6, 2016, which is a continuation application of U.S. patent application Ser. No. 15/144,485, filed May 2, 2016, now U.S. Pat. No. 9,540,386, issued on Jan. 10, 2107, which is a divisional application of U.S. patent application Ser. No. 14/426,630, filed Mar. 6, 2015, now U.S. Pat. No. 9,359,368, issued on Jun. 7, 2016, which is a national phase application under 35 U.S.C. § 371 of International Patent Application No. PCT/JP2013/073865, filed Sep. 5, 2013, which claims priority to Japanese Patent Application No. 2012-195761, filed Sep. 6, 2012, the contents of all of which are hereby incorporated by reference in their entirety.

TECHNICAL FIELD

The present invention relates to crystals of a dispiropyrrolidine compound having anti-tumor activity by inhibition of murine double minute 2 (Mdm2) or a salt thereof.

BACKGROUND ART p53 is known as an important factor for inhibiting canceration of cells. p53 is a transcription factor that induces the expression of genes involved in the cell cycle and cellular apoptosis in response to various stresses. p53 is thought to inhibit canceration of cells by a transcription regulating function thereof. In fact, deletion or mutation of the p53 gene is observed in about half of human cancer cases.

Meanwhile, overexpression of murine double minute 2 (Mdm2), a type of E3 ubiquitin ligase, is known as a factor for canceration of cells that are cancerated in spite of the presence of normal p53. Mdm2 is a protein of which expression is induced by p53. Mdm2 negatively regulates p53 by mediating degradation of p53 by binding to the transcription activity domain of p53 to decrease the transcription activity of p53, exporting p53 out of the nucleus, and further acting as a ubiquitination ligase against p53. Therefore, it is thought that inactivation of functions of and degradation of p53 are promoted in cells in which Mdm2 is overexpressed, resulting in canceration (Non Patent Document 1).

Paying attention to such functions of Mdm2, many approaches have been attempted using substances that inhibit the suppression of p53 functions by Mdm2, as candidate anti-tumor agents. Examples of the Mdm2 inhibitors targeting the Mdm2-p53 binding site have been reported, which include spirooxindole derivatives (Patent Documents 1-15, Non Patent Documents 1-3), indole derivatives (Patent Document 16), pyrrolidine-2-carboxamide derivatives (Patent Document 17), pyrrolidinone derivatives (Patent Document 18) and isoindolinone derivatives (Patent Document 19, Non Patent Document 4).

CITATION LIST

Patent Documents

Patent Document 1: WO2006/091646
Patent Document 2: WO2006/136606
Patent Document 3: WO2007/104664
Patent Document 4: WO2007/104714
Patent Document 5: WO2008/034736
Patent Document 6: WO2008/036168
Patent Document 7: WO2008/055812
Patent Document 8: WO2008/141917
Patent Document 9: WO2008/141975
Patent Document 10: WO2009/077357
Patent Document 11: WO2009/080488
Patent Document 12: WO2010/084097
Patent Document 13: WO2010/091979
Patent Document 14: WO2010/094622
Patent Document 15: WO2010/121995
Patent Document 16: WO2008/119741
Patent Document 17: WO2010/031713
Patent Document 18: WO2010/028862
Patent Document 19: WO2006/024837

Non Patent Documents

Non Patent Document 1: J. Am. Chem. Soc., 2005, 127, 10130-10131
Non Patent Document 2: J. Med. Chem., 2006, 49, 3432-3435
Non Patent Document 3: J. Med. Chem., 2009, 52, 7970-7973
Non Patent Document 4: J. Med. Chem., 2006, 49, 6209-6221

SUMMARY OF INVENTION

Technical Problem

A dispiropyrrolidine derivative exhibits excellent Mdm2 inhibiting activity and is thus expected to be used as a medicament, particularly, as an anticancer agent. In addition, it is of industrially significant importance to find crystals of the derivative.

Solution to Problem

The present inventors have conducted extensive studies to enhance the medical usefulness of a dispiropyrrolidine derivative that exhibits Mdm2 inhibiting activity and has anti-tumor activity and to improve its solid state properties for this purpose. As a result, the present inventors have found crystals of a dispiropyrrolidine derivative represented by the following formula (1) or a salt thereof.

More specifically, the present invention relates to [1] to [14] given below.

[1] A crystal of (3'R, 4'S, 5'R)—N-[(3R, 6S)-6-carbamoyltetrahydro-2H-pyran-3-yl]-6"-chloro-4'-(2-chloro-3-fluoropyridin-4-yl)-4, 4-dimethyl-2"-oxo-1", 2"-dihydrodispiro[cyclohexane-1, 2'-pyrrolidine-3', 3"-indole]-5'-carboxamide represented by the following formula (1) or a salt thereof:

[Formula 1]

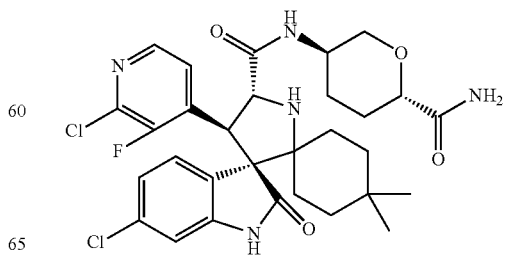

[2] A crystal of a compound as defined in [1] having an X-ray diffraction pattern as shown in FIG. 1 as an X-ray powder diffraction pattern obtained by copper Kα radiation (wavelength λ=1.54 angstroms).

[3] A crystal of a compound as defined in [1] having an X-ray diffraction pattern as shown in FIG. 2 as an X-ray powder diffraction pattern obtained by copper Kα radiation (wavelength λ=1.54 angstroms).

[4] A crystal of a compound as defined in [1] having an X-ray diffraction pattern as shown in FIG. 3 as an X-ray powder diffraction pattern obtained by copper Kα radiation (wavelength λ=1.54 angstroms).

[5] A crystal of a hydrochloride of a compound as defined in [1] having an X-ray diffraction pattern as shown in FIG. 4 as an X-ray powder diffraction pattern obtained by copper Kα radiation (wavelength λ=1.54 angstroms).

[6] A crystal of a methanesulfonate of a compound as defined in [1] having an X-ray diffraction pattern as shown in FIG. 6 as an X-ray powder diffraction pattern obtained by copper Kα radiation (wavelength λ=1.54 angstroms).

[7] A crystal of an ethanesulfonate of a compound as defined in [1] having an X-ray diffraction pattern as shown in FIG. 7 as an X-ray powder diffraction pattern obtained by copper Kα radiation (wavelength λ=1.54 angstroms).

[8] A crystal of a benzenesulfonate of a compound as defined in [1] having an X-ray diffraction pattern as shown in FIG. 8 as an X-ray powder diffraction pattern obtained by copper Kα radiation (wavelength λ=1.54 angstroms).

[9] A crystal of a toluenesulfonate of a compound as defined in [1] having an X-ray diffraction pattern as shown in FIG. 9 as an X-ray powder diffraction pattern obtained by copper Kα radiation (wavelength λ=1.54 angstroms).

[10] A crystal according to [2] exhibiting characteristic peaks at diffraction angles 2θ=7.78, 9.14, 10.06, 10.78, 12.18, 13.42, 14.34, 15.50, 16.62, 17.06, 17.66, 18.18, 18.74, 20.18, 22.46, 24.90, 25.54, 26.94, 27.58, and 28.90 in an X-ray powder diffraction pattern obtained by copper Kα radiation (wavelength λ=1.54 angstroms).

[11] A crystal according to [3] exhibiting characteristic peaks at diffraction angles 2θ=7.62, 13.06, 15.10, 17.22, and 21.98 in an X-ray powder diffraction pattern obtained by copper Kα radiation (wavelength λ=1.54 angstroms).

[12] A crystal according to [4] exhibiting characteristic peaks at diffraction angles 2θ=9.18, 12.18, 15.58, 16.22, 17.22, 18.42, 18.82, and 19.86 in an X-ray powder diffraction pattern obtained by copper Kα radiation (wavelength λ=1.54 angstroms).

[13] A crystal according to [5] exhibiting characteristic peaks at diffraction angles 2θ=6.46, 7.86, 9.12, 13.00, 14.42, 19.32, 20.34, 20.42, and 21.98 in an X-ray powder diffraction pattern obtained by copper Kα radiation (wavelength λ=1.54 angstroms).

[14] A crystal according to [6] exhibiting characteristic peaks at diffraction angles 2θ=7.56, 8.26, 14.00, 16.26, 16.78, 17.72, 18.42, 18.62, 20.28, and 23.06 in an X-ray powder diffraction pattern obtained by copper Kα radiation (wavelength λ=1.54 angstroms).

[15] A crystal according to [7] exhibiting characteristic peaks at diffraction angles 2θ=6.28, 7.72, 12.62, 14.06, 15.50, 16.62, 16.96, 19.68, 21.18, and 25.82 in an X-ray powder diffraction pattern obtained by copper Kα radiation (wavelength λ=1.54 angstroms).

[16] A crystal according to [8] exhibiting characteristic peaks at diffraction angles 2θ=6.22, 7.34, 7.90, 12.46, 13.60, 14.22, 15.56, 18.86, 19.04, 19.52, 19.72, and 20.54 in an X-ray powder diffraction pattern obtained by copper Kα radiation (wavelength λ=1.54 angstroms).

[17] A crystal according to [9] exhibiting characteristic peaks at diffraction angles 2θ=6.16, 7.18, 7.88, 12.38, 13.50, 13.88, 15.46, 18.46, 19.10, 19.28, 19.66, 20.28, 21.88, and 24.68 in an X-ray powder diffraction pattern obtained by copper Kα radiation (wavelength λ=1.54 angstroms).

[18] A medicament comprising a crystal according to any one of [1] to [17].

Advantageous Effects of Invention

The present invention provides crystals of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3', 3"-indole]-5'-carboxamide or a salt thereof having Mdm2 inhibiting activity. The crystals of the present invention have excellent physicochemical properties in solid state and are useful as anti-tumor agents.

BRIEF DESCRIPTION OF DRAWINGS

FIG. 1 shows an X-ray powder diffraction pattern of the crystal (free form) obtained in Example 1-1. In the drawing, the vertical axis represents diffraction intensity indicated in counts/second (cps) units, and the horizontal axis represents diffraction angle indicated in 2θ values.

FIG. 2 shows an X-ray powder diffraction pattern of the crystal (free form) obtained in Example 1-2. In the drawing, the vertical axis represents diffraction intensity indicated in counts/second (cps) units, and the horizontal axis represents diffraction angle indicated in 2θ values.

FIG. 3 shows an X-ray powder diffraction pattern of the crystal (free form) obtained in Example 1-3. In the drawing, the vertical axis represents diffraction intensity indicated in counts/second (cps) units, and the horizontal axis represents diffraction angle indicated in 2θ values.

FIG. 4 shows an X-ray powder diffraction pattern of the crystal (hydrochloride) obtained in Example 2. In the drawing, the vertical axis represents diffraction intensity indicated in counts/second (cps) units, and the horizontal axis represents diffraction angle indicated in 2θ values.

FIG. 5 shows an X-ray powder diffraction pattern of the compound (sulfate) obtained in Example 3. In the drawing, the vertical axis represents diffraction intensity indicated in counts/second (cps) units, and the horizontal axis represents diffraction angle indicated in 2θ values.

FIG. 6 shows an X-ray powder diffraction pattern of the crystal (methanesulfonate) obtained in Example 4. In the drawing, the vertical axis represents diffraction intensity indicated in counts/second (cps) units, and the horizontal axis represents diffraction angle indicated in 2θ values.

FIG. 7 shows an X-ray powder diffraction pattern of the crystal (ethanesulfonate) obtained in Example 5. In the drawing, the vertical axis represents diffraction intensity indicated in counts/second (cps) units, and the horizontal axis represents diffraction angle indicated in 2θ values.

FIG. 8 shows an X-ray powder diffraction pattern of the crystal (benzenesulfonate) obtained in Example 6. In the drawing, the vertical axis represents diffraction intensity indicated in counts/second (cps) units, and the horizontal axis represents diffraction angle indicated in 2θ values.

FIG. 9 shows an X-ray powder diffraction pattern of the crystal (toluenesulfonate) obtained in Example 7. In the drawing, the vertical axis represents diffraction intensity indicated in counts/second (cps) units, and the horizontal axis represents diffraction angle indicated in 2θ values.

FIG. 10 shows adsorption-desorption isotherms of the crystal (free form) obtained in Example 1-1. In the drawing, the vertical axis represents change (%) in the weight of the compound, and the horizontal axis represents humidity (% RH).

FIG. 11 shows adsorption-desorption isotherms of the crystal (free form) obtained in Example 1-2. In the drawing, the vertical axis represents change (%) in the weight of the compound, and the horizontal axis represents humidity (% RH).

FIG. 12 shows adsorption-desorption isotherms of the crystal (hydrochloride) obtained in Example 2. In the drawing, the vertical axis represents change (%) in the weight of the compound, and the horizontal axis represents humidity (% RH).

FIG. 13 shows adsorption-desorption isotherms of the crystal (methanesulfonate) obtained in Example 4. In the drawing, the vertical axis represents change (%) in the weight of the compound, and the horizontal axis represents humidity (% RH).

FIG. 14 shows adsorption-desorption isotherms of the crystal (ethanesulfonate) obtained in Example 5. In the drawing, the vertical axis represents change (%) in the weight of the compound, and the horizontal axis represents humidity (% RH).

FIG. 15 shows adsorption-desorption isotherms of the crystal (benzenesulfonate) obtained in Example 6. In the drawing, the vertical axis represents change (%) in the weight of the compound, and the horizontal axis represents humidity (% RH).

FIG. 16 shows adsorption-desorption isotherms of the crystal (toluenesulfonate) obtained in Example 7. In the drawing, the vertical axis represents change (%) in the weight of the compound, and the horizontal axis represents humidity (% RH).

FIG. 17 is a diagram showing the thermal analysis data of the crystal (free form) obtained in Example 1-1. In the drawing, the vertical axis represents temperature difference (DTA) and weight change (TG), and the horizontal axis represents temperature (° C.). The solid line depicts a DTA curve, and the broken line depicts a TG curve.

FIG. 18 is a diagram showing the thermal analysis data of the crystal (free form) obtained in Example 1-2. In the drawing, the vertical axis represents temperature difference (DTA) and weight change (TG), and the horizontal axis represents temperature (° C.). The solid line depicts a DTA curve, and the broken line depicts a TG curve.

FIG. 19 is a diagram showing the thermal analysis data of the crystal (free form) obtained in Example 1-3. In the drawing, the vertical axis represents temperature difference (DTA) and weight change (TG), and the horizontal axis represents temperature (° C.). The solid line depicts a DTA curve, and the broken line depicts a TG curve.

FIG. 20 is a diagram showing the thermal analysis data of the crystal (hydrochloride) obtained in Example 2. In the drawing, the vertical axis represents temperature difference (DTA) and weight change (TG), and the horizontal axis represents temperature (° C.). The solid line depicts a DTA curve, and the broken line depicts a TG curve.

FIG. 21 is a diagram showing the thermal analysis data of the crystal (methanesulfonate) obtained in Example 4. In the drawing, the vertical axis represents temperature difference (DTA) and weight change (TG), and the horizontal axis represents temperature (° C.). The solid line depicts a DTA curve, and the broken line depicts a TG curve.

FIG. 22 is a diagram showing the thermal analysis data of the crystal (ethanesulfonate) obtained in Example 5. In the drawing, the vertical axis represents temperature difference (DTA) and weight change (TG), and the horizontal axis represents temperature (° C.). The solid line depicts a DTA curve, and the broken line depicts a TG curve.

FIG. 23 is a diagram showing the thermal analysis data of the crystal (benzenesulfonate) obtained in Example 6. In the drawing, the vertical axis represents temperature difference (DTA) and weight change (TG), and the horizontal axis represents temperature (° C.). The solid line depicts a DTA curve, and the broken line depicts a TG curve.

FIG. 24 is a diagram showing the thermal analysis data of the crystal (toluenesulfonate) obtained in Example 7. In the drawing, the vertical axis represents temperature difference (DTA) and weight change (TG), and the horizontal axis represents temperature (° C.). The solid line depicts a DTA curve, and the broken line depicts a TG curve.

DESCRIPTION OF EMBODIMENTS

The present invention relates to crystals of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide represented by the following formula (1):

[Formula 2]

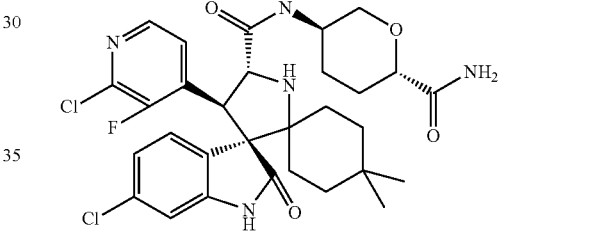

(hereinafter, also referred to as compound (1)) or a salt thereof. In this context, the crystals refer to a solid having three-dimensional regular repeats of atoms (or populations thereof) constituting the internal structure and are discriminated from amorphous solids, which do not have such a regular internal structure.

Examples of a salt of the compound (1) include any of those described in the Examples. The compound (1) or the salt thereof may be present in a free or solvate form. The compound (1) or the salt thereof may be present in a hydrate form, for example, by absorbing moisture in the air. The solvate is not particularly limited so long as it is pharmaceutically acceptable. Specific examples thereof include a hydrate, an ethanol solvate, and a 2-propanol solvate.

Even crystals derived from the same compound may be generated as a plurality of crystals (crystal polymorphs) differing in internal structure and physicochemical properties depending on crystallization conditions. The crystals of the present invention may be any of these crystal polymorphs or may be a mixture of two or more crystal polymorphs.

The crystals of the present invention may have attached water as a result of absorbing moisture when left in the air, or may form a hydrate, for example, by heating to 25 to 150° C. under ordinary atmospheric conditions. In addition, the crystals of the present invention may also have an attached residual solvent or contain a solvent used in crystallization in their solvate.

In the present specification, the crystals of the present invention may be defined on the basis of X-ray powder diffraction data. The X-ray powder diffraction can be carried out by measurement and analysis approaches usually used in the art, and can be performed, for example, by a method described in Examples. In general, hydrates or dehydrates may vary in their lattice constants through the adsorption or desorption of crystal water to cause changes in diffraction angle (2θ) in the X-ray powder diffraction. Also, peak intensity may be changed depending on, for example, difference in crystal growth face or the like (crystal habit). Accordingly, in the case where the crystals of the present invention are defined on the basis of X-ray powder diffraction data, crystals that match therewith in terms of diffraction angles of peaks in the X-ray powder diffraction and X-ray powder diffraction patterns as well as hydrates and dehydrates obtained therefrom are also included in the scope of the present invention.

In a preferred embodiment, a crystal of the present invention is a crystal (free form) having the X-ray powder diffraction pattern shown in FIG. 1 as an X-ray powder diffraction pattern obtained by copper Kα radiation (wavelength λ=1.54 angstroms). Also, the crystal is a crystal exhibiting characteristic peaks at diffraction angles 2θ=7.78, 9.14, 10.06, 10.78, 12.18, 13.42, 14.34, 15.50, 16.62, 17.06, 17.66, 18.18, 18.74, 20.18, 22.46, 24.90, 25.54, 26.94, 27.58, and 28.90 in an X-ray powder diffraction pattern obtained by copper Kα radiation (wavelength λ=1.54 angstroms).

In another preferred embodiment, a crystal of the present invention is a crystal (free form) having the X-ray powder diffraction pattern shown in FIG. 2 as an X-ray powder diffraction pattern obtained by copper Kα radiation (wavelength λ=1.54 angstroms). Also, the crystal is a crystal exhibiting characteristic peaks at diffraction angles 2θ=7.62, 13.06, 15.10, 17.22, and 21.98 in an X-ray powder diffraction pattern obtained by copper Kα radiation (wavelength λ=1.54 angstroms).

In another preferred embodiment, a crystal of the present invention is a crystal (free form) having the X-ray powder diffraction pattern shown in FIG. 3 as an X-ray powder diffraction pattern obtained by copper Kα radiation (wavelength λ=1.54 angstroms). Also, the crystal is a crystal exhibiting characteristic peaks at diffraction angles 2θ=9.18, 12.18, 15.58, 16.22, 17.22, 18.42, 18.82, and 19.86 in an X-ray powder diffraction pattern obtained by copper Kα radiation (wavelength λ=1.54 angstroms).

In another preferred embodiment, a crystal of the present invention is a crystal (hydrochloride) having the X-ray powder diffraction pattern shown in FIG. 4 as an X-ray powder diffraction pattern obtained by copper Kα radiation (wavelength λ=1.54 angstroms). Also, the crystal is a crystal exhibiting characteristic peaks at diffraction angles 2θ=6.46, 7.86, 9.12, 13.00, 14.42, 19.32, 20.34, 20.42, and 21.98 in an X-ray powder diffraction pattern obtained by copper Kα radiation (wavelength λ=1.54 angstroms).

In another preferred embodiment, a crystal of the present invention is a crystal (methanesulfonate) having the X-ray powder diffraction pattern shown in FIG. 6 as an X-ray powder diffraction pattern obtained by copper Kα radiation (wavelength λ=1.54 angstroms). Also, the crystal is a crystal exhibiting characteristic peaks at diffraction angles 2θ=7.56, 8.26, 14.00, 16.26, 16.78, 17.72, 18.42, 18.62, 20.28, and 23.06 in an X-ray powder diffraction pattern obtained by copper Kα radiation (wavelength λ=1.54 angstroms).

In another preferred embodiment, a crystal of the present invention is a crystal (ethanesulfonate) having the X-ray powder diffraction pattern shown in FIG. 7 as an X-ray powder diffraction pattern obtained by copper Kα radiation (wavelength λ=1.54 angstroms). Also, the crystal is a crystal exhibiting characteristic peaks at diffraction angles 2θ=6.28, 7.72, 12.62, 14.06, 15.50, 16.62, 16.96.19.68.21.18, and 25.82 in an X-ray powder diffraction pattern obtained by copper Kα radiation (wavelength λ=1.54 angstroms).

In another preferred embodiment, a crystal of the present invention is a crystal (benzenesulfonate) having the X-ray powder diffraction pattern shown in FIG. 8 as an X-ray powder diffraction pattern obtained by copper Kα radiation (wavelength λ=1.54 angstroms). Also, the crystal is a crystal exhibiting characteristic peaks at diffraction angles 2θ=6.22, 7.34, 7.90, 12.46, 13.60, 14.22, 15.56, 18.86, 19.04, 19.52, 19.72, and 20.54 in an X-ray powder diffraction pattern obtained by copper Kα radiation (wavelength λ=1.54 angstroms).

In another preferred embodiment, a crystal of the present invention is a crystal (toluenesulfonate) having the X-ray powder diffraction pattern shown in FIG. 9 as an X-ray powder diffraction pattern obtained by copper Kα radiation (wavelength λ=1.54 angstroms). Also, the crystal is a crystal exhibiting characteristic peaks at diffraction angles 2θ=6.16, 7.18, 7.88, 12.38, 13.50, 13.88, 15.46, 18.46, 19.10, 19.28, 19.66, 20.28, 21.88, and 24.68 in an X-ray powder diffraction pattern obtained by copper Kα radiation (wavelength λ=1.54 angstroms).

According to another aspect, the present invention relates to a medicament comprising a crystal of the present invention as an active ingredient.

The medicament comprising a crystal of the present invention as an active ingredient is preferably provided in the form of a pharmaceutical composition comprising a crystal of the present invention and one or two or more pharmaceutically acceptable carriers. The medicament of the present invention is not particularly limited by dosage form and can be administered orally or parenterally. Preferably, the medicament of the present invention is orally administered.

The pharmaceutical composition of the present invention comprises a crystal of the present invention as at least a portion of the compound (I). The pharmaceutical composition may contain a crystal form of the compound (I) other than the crystals of the present invention. The content of a crystal of the present invention in the pharmaceutical composition can be in the range from 0.01% by weight to 99.9% by weight with respect to the whole compound (I) in the pharmaceutical composition, for example, 0.01% by weight or larger, 0.05% by weight or larger, 0.1% by weight or larger, 0.5% by weight or larger, 1% by weight or larger, 2% by weight or larger, 3% by weight or larger, 4% by weight or larger, 5% by weight or larger, 10% by weight or larger, 20% by weight or larger, 30% by weight or larger, 40% by weight or larger, 50% by weight or larger, 60% by weight or larger, 70% by weight or larger, 80% by weight or larger, 90% by weight or larger, 95% by weight or larger, 96% by weight or larger, 97% by weight or larger, 98% by weight or larger, 99% by weight or larger, 99.5% by weight or larger, 99.6% by weight or larger, 99.7% by weight or larger, 99.8% by weight or larger, or 99.9% by weight or larger. The presence or absence of a crystal of the present invention in the pharmaceutical composition can be confirmed by an instrumental analysis method (e.g., X-ray powder diffraction, thermal analysis, or infrared absorption spectra) described in the present specification.

The crystals of the present invention can be used as an inhibitor of Mdm2 and can be used as a medicament, particularly preferably an anticancer agent, comprising the crystals of the present invention.

In one embodiment of the present invention, a crystal of the present invention can be used as a p53-Mdm2 binding inhibitor and/or an Mdm2 ubiquitin ligase inhibitor because the compound (1) inhibits the binding of p53 with Mdm2 and the ubiquitination of p53 by Mdm2.

The condition of the p53-Mdm2 binding can be examined by a method conventionally used by those skilled in the art to examine binding conditions between proteins (for example, immunological techniques, surface plasmon resonance techniques, etc.). Examples of methods for examining the condition of the Mdm2-p53 binding using an immunological technique include an immuno-sedimentation method and enzyme-linked-immuno-sorbent assay (ELISA). An antibody used in such immunological techniques may be an anti-Mdm2 antibody and/or an anti-p53 antibody that can directly detect Mdm2 and/or p53. When Mdm2 and/or p53 is labeled with a tag (for example, a GST tag or a histidine tag) or the like, an antibody suitable for labeling (for example, an anti-GST antibody or an anti-histidine antibody) can be used. Methods for examining the condition of the Mdm2-p53 binding using an immunological technique are described in, for example, WO2003/51359, WO2003/51360, U.S. Patent Application Publication No. 2004/259867 or 2004/259884, and WO2005/110996. Methods for examining the condition of the Mdm2-p53 binding using a surface plasmon resonance technique are described in, for example, Science, vol. 303, p. 844-848, 2004.

Ubiquitin ligase activity of Mdm2 against p53 can be examined by an ubiquitin ligase assay conventionally used by those skilled in the art. The ubiquitin ligase activity can be detected by, for example, comparing ubiquitination of p53 by ubiquitin activation enzyme (E1), ubiquitin binding enzyme (E2), and ubiquitin ligase (E3) (Mdm2) in the presence and absence of a test compound (for example, refer to WO2001/75145 and WO2003/76608).

In another embodiment, a crystal of the present invention can be used as an inhibitor of suppression of the p53 transcription activity because the compound (1) restores functions of p53 as a transcription factor that is suppressed by Mdm2 by inhibiting the binding of Mdm2 to the p53 transcription activation domain. The inhibitor of suppression of the p53 transcription activity can be obtained by, for example, measuring the mRNA level or the protein level of a protein whose transcription is regulated by p53 (for example, p21$^{Waf1/Cip1}$) in the presence or absence of a test compound by an mRNA measuring method (for example, Northern blot) or a protein measuring method (for example, Western blot) conventionally used by those skilled in the art and selecting the test compound as an inhibitor of suppression of the p53 transcription activity when the mRNA level or the protein level is increased in the presence of the test compound as compared with that in the absence of the test compound. Furthermore, the inhibitor of suppression of the p53 transcription activity can also be identified by a reporter assay using the reporter activity of a reporter gene including a p53 responsive element as an indicator.

In another embodiment, a crystal of the present invention can be used as a p53 degradation inhibitor because the compound (1) inhibits ubiquitination of p53 by Mdm2 and thereby prevents the degradation of p53 in proteasomes. The p53 degradation inhibitor can be obtained by, for example, measuring the protein level of p53 in the presence or absence of a test compound by a protein measuring method (for example, Western blot) conventionally used by those skilled in the art and selecting the test compound as a p53 degradation inhibitor when the protein level is increased in the presence of the test compound as compared with that in the absence of the test compound.

In another embodiment, a crystal of the present invention can be used as an anti-tumor agent because the compound (1) normalizes functions of p53 as a cancer-restraining gene by inhibition of the Mdm2-p53 binding and/or ubiquitination of p53 by Mdm2.

Cellular growth inhibiting activity can be examined by methods for testing growth inhibition conventionally used by those skilled in the art. The cell growth inhibition activity can be determined by, for example, comparing the levels of cellular growth (for example, tumor cells) in the presence or absence of a test compound as described in the following Test Example 2. The levels of cellular growth can be examined by using, for example, a test system for measuring living cells. Examples of the method for measuring living cells include the [$^3$H]-thymidine uptake test, the BrdU method, the MTT assay, and so forth.

Moreover, in vivo anti-tumor activity can be examined by methods for testing anti-tumor activity conventionally used by those skilled in the art. The in vivo anti-tumor activity of the present invention can be confirmed by, for example, transplanting various tumor cells to mice, rats, or the like; after confirming the engraftment of the transplanted cells, orally or intravenously administering the compound of the present invention to the animals; a few days or a few weeks later, comparing tumor growth in a drug-non-administered group with that in the compound-administered group.

A crystal of the present invention can be used for the treatment of tumors or cancers, for example, lung cancer, digestive system cancer, ovary cancer, uterine cancer, breast cancer, prostate cancer, liver cancer, head/neck region cancer, blood cancer, renal cancer, skin cancer (malignant melanoma, etc.), retinoblastoma, testicular tumors, and sarcoma, more preferably lung cancer, breast cancer, prostate cancer, colon cancer, acute myeloid leukemia, malignant lymphoma, malignant melanoma, retinoblastoma, neuroblastoma, and sarcoma. However, the present invention is not limited to these cancers.

A medicament of the present invention can contain a crystal of the present invention and a pharmaceutically acceptable carrier and can be administered as various injections such as intravenous injection, intramuscular injection, and subcutaneous injection or by various methods such as oral administration or percutaneous administration. Pharmaceutically acceptable carrier means a pharmacologically acceptable material (for example, an excipient, a diluent, an additive, a solvent, etc.) that is involved in transport of a composition containing a crystal of the present invention from a given organ to another organ.

A formulation can be prepared by selecting a suitable formulation form (for example, oral formulation or injection) depending on the administration method and using various conventionally used methods for preparing a formulation. Examples of oral formulations include tablets, powders, granules, capsules, pills, lozenges, solutions, syrups, elixirs, emulsions, oily or aqueous suspensions, and so forth. In oral administration, the free compound or a salt form may be used. An aqueous formulation can be prepared by forming an acid adduct with a pharmacologically acceptable acid or by forming an alkali metal salt such as sodium. As an injection, a stabilizer, a preservative, a dissolving aid, and the like can be used in the formulation. After filling a solution that may contain these aids and the like in a vessel, a formulation for use may be prepared as a solid formulation by lyophilization or the like. Furthermore, one dose may be filled in one vessel, or two or more doses may be filled in a vessel.

Examples of solid formulations include tablets, powders, granules, capsules, pills, and lozenges. These solid formulations may contain pharmaceutically acceptable additives together with a crystal of the present invention. Examples of additives include fillers, extenders, binders, disintegrating agents, dissolution promoting agents, skin wetting agents, and lubricants, and these can be selected and mixed as required to prepare a formulation.

Examples of liquid formulations include solutions, syrups, elixirs, emulsions, and suspensions. These liquid formulations may contain pharmaceutically acceptable additives together with a crystal of the present invention. Examples of additives include suspending agents and emulsifiers, and these are selected and mixed as required to prepare a formulation.

A crystal of the present invention can be used in cancer treatment of mammals, in particular, humans. The dose and the administration interval can be suitably selected depending on the site of the disease, the patient's height, body weight, sex, or medical history, according to a physician's judgment. When the compound of the present invention is administered to a human, the dose range is approx. 0.01 to 500 mg/kg body weight per day, preferably, approx. 0.1 to 100 mg/kg body weight. Preferably, the compound of the present invention is administered to a human once a day, or the dose is divided two to four times, and administration is repeated at an appropriate interval. Furthermore, the daily dose may exceed the above-mentioned dose at a physician's discretion, if necessary.

A crystal of the present invention may be used in combination with an additional anti-tumor agent. Examples thereof include anti-tumor antibiotics, anti-tumor plant constituents, BRMs (biological response modifiers), hormones, vitamins, anti-tumor antibodies, molecular target drugs, and other anti-tumor agents.

More specifically, examples of alkylating agents include: alkylating agents such as nitrogen mustard, nitrogen mustard N-oxide, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin, and ranimustine; and busulfan, improsulfan tosylate, and dacarbazine.

Examples of various metabolic antagonists include: purine metabolic antagonists such as 6-mercaptopurine, 6-thioguanine, and thioinosine; pyrimidine metabolic antagonists such as fluorouracil, tegafur, tegafur-uracil, carmofur, doxifluridine, broxuridine, cytarabine, and enocitabine; and folic acid metabolic antagonists such as methotrexate and trimetrexate.

Examples of anti-tumor antibiotics include: anti-tumor anthracycline antibiotics such as mitomycin C, bleomycin, peplomycin, daunorubicin, aclarubicin, doxorubicin, pirarubicin, THP-adriamycin, 4'-epidoxorubicin, and epirubicin; and chromomycin A3 and actinomycin D.

Examples of anti-tumor plant constituents include: vinca alkaloids such as vindesine, vincristine, and vinblastine; taxanes such as paclitaxel and docetaxel; and epipodophyllotoxins such as etoposide and teniposide.

Examples of BRMs include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethinylestradiol, chlormadinone, and medroxyprogesterone.

Examples of vitamins include vitamin C and vitamin A.

Examples of anti-tumor antibodies and molecular target drugs include trastuzumab, rituximab, cetuximab, nimotuzumab, denosumab, bevacizumab, infliximab, imatinib mesylate, gefitinib, erlotinib, sunitinib, lapatinib, and sorafenib.

Examples of other anti-tumor agents include cisplatin, carboplatin, oxaliplatin, tamoxifen, camptothecin, ifosfamide, cyclophosphamide, melphalan, L-asparaginase, aceglatone, sizofiran, picibanil, procarbazine, pipobroman, neocarzinostatin, hydroxyurea, ubenimex, and krestin.

The present invention also includes a method for preventing and/or treating cancer, comprising administering a crystal of the present invention.

The starting material (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydro-dispiro[cyclohexane-1,2'-pyrrolidine-3',3"-indole]-5'-carboxamide or a salt thereof for the crystals of the present invention can be produced, for example, according to Examples mentioned below.

The X-ray powder diffraction measurement was carried out in Example 1 at a Cu Kα wavelength of λ=1.54 angstroms by a transmission method using D8 Discover with GADDS CST (Bruker Axs K.K.) (tube voltage: 40 kV, tube current: 40 mA, scanning range: 2 to 40, scanning rate: 20°/min). The X-ray powder diffraction measurement was carried out in the other Examples at a Cu Kα wavelength of λ=1.54 angstroms using a reflection-type X-ray powder diffraction apparatus (RINT-TTR III, manufactured by Rigaku Corp.) and a reflection-free sample holder for samples (tube voltage: 50 kV, tube current: 300 mA, scanning range: 2 to 400, scanning rate: 20°/min, sampling width: 0.02°, rotational speed: 120 rpm).

The adsorption and desorption measurement apparatuses used were TA instruments SGA-CX (Examples 2, 6, and 7) and TA instruments VTI-SA (Examples 1, 4, and 5) (temperature: 25° C., humidity: 40, 60, 70, 80, 90, 80, 70, 60, 40, 20, 10, 20, 40, 60, 70% RH).

The thermal analysis (TG/DTA) employed TG/DTA6200 manufactured by SII Nanotechnology Inc. (rate of temperature rise: 10° C./min, ambient gas: nitrogen, nitrogen gas flow rate: 200 mL/min).

EXAMPLES

Example 1

[Formula 3]

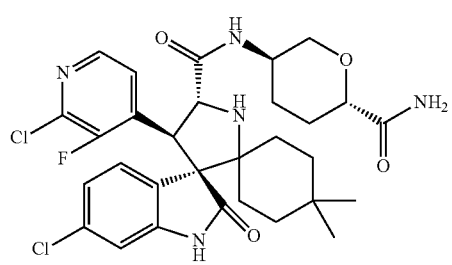

(3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide The compound (35 mg, 0.24 mmol) obtained in Step 3 of Reference Example 2, triethylamine (0.04 ml, 0.30 mmol), 1-hydroxybenzotriazole (27 mg, 0.20 mmol), and 1-ethyl-3-(3-dimethylaminopropyl)carbodiimide hydrochloride (46 mg, 0.24 mmol) were added to a N,N-dimethylformamide (4 ml) solution of the compound (100 mg, 0.20 mmol) obtained in Step 3 of Reference Example 1 and the resulting mixture was stirred at 50° C. for 1 hour. After cooling, the reaction mixture was diluted with ethyl acetate, washed with water, saturated sodium bicarbonate solution, and brine in this order and then dried over anhydrous sodium sulfate. The solvent was evaporated under reduced pressure, then the residue was purified by NH-silica gel column chromatography [chloroform:methanol=50:1 (v/v)] and the purified product obtained was dissolved in methanol (10 ml) and stirred at 60° C. for 24 hours. The solvent was evaporated under reduced pressure to give 94 mg (76%) of the title compound as a solid.

$^1$H-NMR (400 MHz, CDCl$_3$) δ: 0.68 (3H, s), 0.95 (3H, s), 1.11-1.27 (2H, m), 1.35-1.81 (8H, m), 2.10-2.17 (1H, m), 2.25-2.32 (1H, m), 3.15 (1H, t, J=10.5 Hz), 3.27 (1H, br s), 3.80 (1H, dd, J=11.0, 2.3 Hz), 3.85-3.95 (1H, m), 4.13 (1H, ddd, J=10.8, 4.5, 1.3 Hz), 4.44 (1H, d, J=9.2 Hz), 4.64 (1H, d, J=9.2 Hz), 5.46 (1H, d, J=3.7 Hz), 6.49 (1H, d, J=3.7 Hz), 6.74 (1H, d, J=1.8 Hz), 7.07 (1H, dd, J=8.2, 1.8 Hz), 7.31 (1H, dd, J=8.2, 2.3 Hz), 7.48-7.52 (2H, m), 7.62 (1H, s), 8.05 (1H, d, J=5.5 Hz).

MS (ESI) m/z: 618 (M+H)$^+$.

Example 1-1

A trichloroethylene/ethanol mixture (95/5) (4.75 ml) was added to the compound (302 mg, 0.49 mmol) obtained in Example 1 and then the resulting mixture was heated to approximately 50° C. for dissolution. The reaction mixture was left standing at room temperature to precipitate a crystal. The precipitated crystal was collected by filtration and dried at room temperature to give a crystal. The crystal was subjected to the measurement of X-ray powder diffraction, simultaneous thermogravimetry and differential thermal analysis (TG/DTA), and adsorption and desorption behaviors.

Alternatively, the crystal can also be obtained using ethyl formate and acetonitrile.

The X-ray powder diffraction pattern is shown in FIG. 1, the adsorption-desorption isotherms are shown in FIG. 10, and the thermal analysis data (TG/DTA) are shown in FIG. 17.

TABLE 1

Peak of X-ray powder diffraction pattern (relative intensity of 22 or more)

| Peak number | 2θ | d value | Relative intensity |
|---|---|---|---|
| 1 | 7.78 | 11.35 | 28 |
| 2 | 9.14 | 9.66 | 72 |
| 3 | 10.06 | 8.78 | 22 |
| 4 | 10.78 | 8.20 | 39 |
| 5 | 12.18 | 7.26 | 67 |
| 6 | 13.42 | 6.59 | 26 |

TABLE 1-continued

Peak of X-ray powder diffraction pattern (relative intensity of 22 or more)

| Peak number | 2θ | d value | Relative intensity |
|---|---|---|---|
| 7 | 14.34 | 6.17 | 23 |
| 8 | 15.50 | 5.71 | 43 |
| 9 | 16.62 | 5.33 | 24 |
| 10 | 17.06 | 5.19 | 32 |
| 11 | 17.66 | 5.02 | 28 |
| 12 | 18.18 | 4.87 | 77 |
| 13 | 18.74 | 4.73 | 100 |
| 14 | 20.18 | 4.40 | 72 |
| 15 | 22.46 | 3.95 | 30 |
| 16 | 24.90 | 3.57 | 34 |
| 17 | 25.54 | 3.48 | 33 |
| 18 | 26.94 | 3.31 | 25 |
| 19 | 27.58 | 3.23 | 27 |
| 20 | 28.90 | 3.09 | 27 |

Example 1-2

Methanol (3.6 ml) was added to the compound (301 mg, 0.49 mmol) obtained in Example 1 and then the resulting mixture was heated to approximately 50° C. for dissolution. The reaction mixture was left standing at room temperature to precipitate a crystal. The precipitated crystal was collected by filtration and dried at room temperature to give a crystal. The crystal was subjected to the measurement of X-ray powder diffraction, TG/DTA, and adsorption and desorption behaviors.

Alternatively, the crystal can also be obtained using 2-butanone.

The X-ray powder diffraction pattern is shown in FIG. 2, the adsorption-desorption isotherms are shown in FIG. 11, and the thermal analysis data (TG/DTA) are shown in FIG. 18.

TABLE 2

Peak of X-ray powder diffraction pattern (relative intensity of 14 or more)

| Peak number | 2θ | d value | Relative intensity |
|---|---|---|---|
| 1 | 7.62 | 11.59 | 100 |
| 2 | 13.06 | 6.77 | 14 |
| 3 | 15.10 | 5.86 | 47 |
| 4 | 17.22 | 5.14 | 27 |
| 5 | 21.98 | 4.04 | 19 |

Example 1-3

Trichloroethylene (1.5 ml) was added to the compound (100 mg, 0.16 mmol) obtained in Example 1 and then the resulting mixture was heated to approximately 50° C. for dissolution. The reaction mixture was left standing at room temperature to precipitate a crystal. The precipitated crystal was collected by filtration and dried at room temperature to give a crystal. The crystal was subjected to the measurement of X-ray powder diffraction and TG/DTA.

The X-ray powder diffraction pattern is shown in FIG. 3, and the thermal analysis data (TG/DTA) are shown in FIG. 19.

TABLE 3

Peak of X-ray powder diffraction pattern (relative intensity of 44 or more)

| Peak number | 2θ | d value | Relative intensity |
|---|---|---|---|
| 1 | 9.18 | 9.62 | 100 |
| 2 | 12.18 | 7.26 | 58 |
| 3 | 15.58 | 5.68 | 44 |
| 4 | 16.22 | 5.46 | 48 |
| 5 | 17.22 | 5.14 | 54 |
| 6 | 18.42 | 4.81 | 73 |
| 7 | 18.82 | 4.71 | 66 |
| 8 | 19.86 | 4.47 | 49 |

Example 2

A Crystal of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide hydrochloride water/2-propanol (IPA) solvate Concentrated hydrochloric acid (0.026 ml, 0.31 mmol) was added to a 2-propanol (2.0 ml) solution of the compound (192 mg, 0.31 mmol) obtained in Example 1 and then the resulting mixture was stirred at room temperature for 18 hours. The precipitate was collected by filtration to give 173 mg (85%) of the title crystal.

$^1$H-NMR (500 MHz, DMSO-d$_6$) δ: 0.62 (3H, s), 0.92 (3H, s), 1.09-1.58 (6H, m), 1.65-2.07 (5H, m), 2.53-2.94 (1H, m), 3.29-3.73 (5H, m), 4.56-4.76 (1H, m), 4.85-5.23 (1H, m), 6.80 (1H, s), 7.01-7.13 (2H, m), 7.14-7.20 (1H, m), 7.49-7.74 (2H, m), 8.19-8.42 (1H, m), 8.61-9.08 (1H, m), 10.41 (1H, br s), 11.25 (1H, br s).

Anal. Calcd for $C_{30}H_{34}Cl_2FN_5O_4 \cdot HCl \cdot 0.75H_2O \cdot IPA$: C, 54.48; H, 6.03; N, 9.63. Found: C, 54.47; H, 6.14; N, 9.65.

The X-ray powder diffraction pattern of the title crystal is shown in FIG. 4, the adsorption-desorption isotherms thereof are shown in FIG. 12, and the thermal analysis data (TG/DTA) thereof are shown in FIG. 20.

TABLE 4

Peak of X-ray powder diffraction pattern (relative intensity of 15 or more)

| Peak number | 2θ | d value | Relative intensity |
|---|---|---|---|
| 1 | 6.46 | 13.67 | 35 |
| 2 | 7.86 | 11.24 | 100 |
| 3 | 9.12 | 9.69 | 17 |
| 4 | 13.00 | 6.80 | 15 |
| 5 | 14.42 | 6.14 | 29 |
| 6 | 19.32 | 4.59 | 17 |
| 7 | 20.34 | 4.36 | 29 |
| 8 | 20.42 | 4.35 | 28 |
| 9 | 21.98 | 4.04 | 16 |

Example 3

(3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide sulfate water/2-propanol (IPA) solvate Concentrated sulfuric acid (0.005 ml, 0.08 mmol) was added to a 2-propanol (0.5 ml) solution of the compound (52 mg, 0.08 mmol) obtained in Example 1 and then the resulting mixture was stirred at room temperature for 2 days. The precipitate was collected by filtration to give 20 mg (34%) of the title compound as a solid.

$^1$H-NMR (500 MHz, DMSO-d$_6$) δ: 0.62 (3H, s), 0.92 (3H, s), 1.13-1.61 (6H, m), 1.67-2.09 (5H, m), 2.45-2.88 (1H, m), 3.47-4.01 (5H, m), 4.58-4.77 (1H, m), 4.83-5.11 (1H, m), 6.79 (1H, s), 6.98-7.25 (3H, m), 7.51-7.73 (2H, m), 8.20-8.41 (1H, m), 8.51-8.73 (1H, m), 8.79-9.05 (1H, m), 10.35 (1H, br s), 11.18 (1H, br s).

Anal. Calcd for $C_{30}H_{34}Cl_2FN_5O_4 \cdot H_2SO_4 \cdot 0.25H_2O \cdot IPA$: C, 49.94; H, 5.71; N, 8.82. Found: C, 49.74; H, 5.71; N, 8.85.

The X-ray powder diffraction pattern of the title compound is shown in FIG. 5.

Example 4

(3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide methanesulfonate hydrate crystal Methanesulfonic acid (0.026 ml, 0.39 mmol) was added to a 2-propanol (3 ml) solution of the compound (221 mg, 0.36 mmol) obtained in Example 1 and then the resulting mixture was stirred at room temperature for 16 hours. The precipitate was collected by filtration to give 48 mg (19%) of the title crystal.

$^1$H-NMR (400 MHz, DMSO-d$_6$) δ: 0.62 (3H, s), 0.92 (3H, s), 1.03-2.01 (11H, m), 2.30 (3H, s), 2.47-2.56 (1H, m), 3.72-3.65 (4H, m), 4.62-4.75 (1H, m), 5.95-5.09 (1H, m), 6.73-6.85 (1H, m), 7.04-7.20 (3H, m), 7.54-7.73 (2H, m), 8.23-8.36 (1H, m), 8.60-8.75 (1H, m), 8.83-8.98 (1H, m), 10.83 (1H, br s), 11.22 (1H, br s).

Anal. Calcd for $C_{30}H_{34}Cl_2FN_5O_4 \cdot CH_3SO_3H \cdot 2H_2O$: C, 49.60; H, 5.64; N, 9.33. Found: C, 49.63; H, 5.45; N, 9.30.

The X-ray powder diffraction pattern of the title crystal is shown in FIG. 6, the adsorption-desorption isotherms thereof are shown in FIG. 13, and the thermal analysis data (TG/DTA) thereof are shown in FIG. 21.

TABLE 5

Peak of X-ray powder diffraction pattern (relative intensity of 31 or more)

| Peak number | 2θ | d value | Relative intensity |
|---|---|---|---|
| 1 | 7.56 | 11.68 | 48 |
| 2 | 8.26 | 10.70 | 31 |
| 3 | 14.00 | 6.32 | 100 |
| 4 | 16.26 | 5.45 | 47 |
| 5 | 16.78 | 5.28 | 67 |
| 6 | 17.72 | 5.00 | 65 |
| 7 | 18.42 | 4.81 | 42 |
| 8 | 18.62 | 4.76 | 42 |
| 9 | 20.28 | 4.38 | 94 |
| 10 | 23.06 | 3.85 | 37 |

Example 5

(3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide ethanesulfonate hydrate crystal Ethanesulfonic acid (0.032 ml, 0.39 mmol) was added to a 2-propanol (3 ml) solution of the compound (221 mg, 0.36 mmol) obtained in Example 1 and then the resulting mixture was stirred at room temperature for 23 hours. The precipitate was collected by filtration to give 128 mg (49%) of the title crystal.

$^1$H-NMR (400 MHz, DMSO-$d_6$) δ: 0.62 (3H, s), 0.92 (3H, s), 1.05 (3H, t, J=7.4 Hz), 1.09-1.59 (6H, m), 1.62-2.06 (5H, m), 2.38 (2H, q, J=7.4 Hz), 2.59-3.07 (1H, m), 3.27-3.79 (5H, m), 4.53-4.76 (1H, m), 4.78-5.16 (1H, m), 6.79 (1H, s), 7.00-7.23 (3H, m), 7.51-7.75 (2H, m), 8.21-8.41 (1H, m), 8.48-9.07 (1H, m), 10.35 (1H, br s), 11.19 (1H, br s).

Anal. Calcd for $C_{30}H_{34}Cl_2FN_5O_5O_4 \cdot C_2H_5SO_3H \cdot 4H_2O$: C, 48.00; H, 6.04; N, 8.75. Found: C, 47.97; H, 5.93; N, 8.56.

The X-ray powder diffraction pattern of the title crystal is shown in FIG. 7, the adsorption-desorption isotherms thereof are shown in FIG. 14, and the thermal analysis data (TG/DTA) thereof are shown in FIG. 22.

TABLE 6

Peak of X-ray powder diffraction pattern (relative intensity of 23 or more)

| Peak number | 2θ | d value | Relative intensity |
|---|---|---|---|
| 1 | 6.28 | 14.06 | 100 |
| 2 | 7.72 | 11.44 | 39 |
| 3 | 12.62 | 7.01 | 39 |
| 4 | 14.06 | 6.29 | 36 |
| 5 | 15.50 | 5.71 | 23 |
| 6 | 16.62 | 5.33 | 28 |
| 7 | 16.96 | 5.22 | 32 |
| 8 | 19.68 | 4.51 | 36 |
| 9 | 21.18 | 4.19 | 38 |
| 10 | 25.82 | 3.45 | 24 |

Example 6

(3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro [cyclohexane-1,2'-pyrrolidine-3',3"-indole]-5'-carboxamide benzenesulfonate hydrate crystal Benzenesulfonic acid monohydrate (30 mg, 0.17 mmol) was added to a 2-propanol (1 ml) solution of the compound (104 mg, 0.17 mmol) obtained in Example 1 and then the resulting mixture was stirred at room temperature for 24 hours. The precipitate was collected by filtration to give 116 mg (89%) of the title crystal.

$^1$H-NMR (400 MHz, CDCl$_3$) δ: 0.69 (3H, s), 0.88 (3H, s), 1.09-1.85 (7H, m), 1.88-2.19 (4H, m), 2.53-2.77 (1H, m), 2.95-3.10 (1H, m), 3.53-3.69 (1H, m), 3.71-3.89 (2H, m), 4.68-4.85 (1H, m), 5.47-5.80 (2H, m), 6.52 (1H, s), 6.77-6.90 (1H, m), 7.03-7.11 (1H, m), 7.24-7.44 (5H, m), 7.63-7.98 (4H, m), 8.09-8.43 (1H, m), 10.16 (1H, br s), 10.96 (1H, br s).

Anal. Calcd for $C_{30}H_{34}Cl_2FN_5O_4 \cdot C_6H_5SO_3H \cdot 1.5H_2O$: C, 53.80; H, 5.39; N, 8.71. Found: C, 53.89; H, 5.40; N, 8.80.

The X-ray powder diffraction pattern of the title crystal is shown in FIG. 8, the adsorption-desorption isotherms thereof are shown in FIG. 15, and the thermal analysis data (TG/DTA) thereof are shown in FIG. 23.

TABLE 7

Peak of X-ray powder diffraction pattern (relative intensity of 16 or more)

| Peak number | 2θ | d value | Relative intensity |
|---|---|---|---|
| 1 | 6.22 | 14.20 | 25 |
| 2 | 7.34 | 12.03 | 100 |
| 3 | 7.90 | 11.18 | 50 |
| 4 | 12.46 | 7.10 | 18 |
| 5 | 13.60 | 6.51 | 16 |
| 6 | 14.22 | 6.22 | 16 |
| 7 | 15.56 | 5.69 | 22 |
| 8 | 18.86 | 4.70 | 16 |
| 9 | 19.04 | 4.66 | 16 |
| 10 | 19.52 | 4.54 | 19 |
| 11 | 19.72 | 4.50 | 23 |
| 12 | 20.54 | 4.32 | 20 |

Example 7

(3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro [cyclohexane-1,2'-pyrrolidine-3',3"-indole]-5'-carboxamide p-toluenesulfonate hydrate crystal An acetonitrile (4 ml) solution of p-toluenesulfonic acid monohydrate (85 mg, 0.45 mmol) was added to an acetonitrile (4 ml) suspension of the compound (300 mg, 0.50 mmol) obtained in Example 1 and then the resulting mixture was heated at approximately 50° C. for dissolution. The reaction mixture was stirred at room temperature for 1 day. The precipitate was collected by filtration to give 255 mg (66%) of the title crystal.

$^1$H-NMR (400 MHz, DMSO-$d_6$) δ: 0.63 (3H, s), 0.92 (3H, s), 1.09-1.59 (6H, m), 1.66-2.03 (5H, m), 2.29 (3H, s), 2.70-2.91 (1H, m), 3.34-3.74 (5H, m), 4.67 (1H, d, J=10.1 Hz), 4.80-5.11 (1H, m), 6.80 (1H, s), 7.02-7.22 (5H, m), 7.43-7.52 (2H, m), 7.55-7.70 (2H, m), 8.23-8.39 (1H, m), 8.45-8.74 (1H, m), 10.33 (1H, br s), 11.14 (1H, br s).

Anal. Calcd for $C_{30}H_{34}Cl_2FN_5O_4 \cdot C_6H_4CH_3SO_3H \cdot 1.5H_2O$: C, 54.34; H, 5.55; N, 8.56. Found: C, 54.06; H, 5.45; N, 8.50.

The X-ray powder diffraction pattern of the title crystal is shown in FIG. 9, the adsorption-desorption isotherms thereof are shown in FIG. 16, and the thermal analysis data (TG/DTA) thereof are shown in FIG. 24.

TABLE 8

Peak of X-ray powder diffraction pattern (relative intensity of 17 or more)

| Peak number | 2θ | d value | Relative intensity |
|---|---|---|---|
| 1 | 6.16 | 14.34 | 23 |
| 2 | 7.18 | 12.30 | 100 |
| 3 | 7.88 | 11.21 | 48 |
| 4 | 12.38 | 7.14 | 18 |
| 5 | 13.50 | 6.55 | 22 |
| 6 | 13.88 | 6.37 | 23 |
| 7 | 15.46 | 5.73 | 25 |
| 8 | 18.46 | 4.80 | 21 |
| 9 | 19.10 | 4.64 | 27 |
| 10 | 19.28 | 4.60 | 19 |
| 11 | 19.66 | 4.51 | 22 |
| 12 | 20.28 | 4.38 | 32 |
| 13 | 21.88 | 4.06 | 17 |
| 14 | 24.68 | 3.60 | 19 |

Reference Example 1

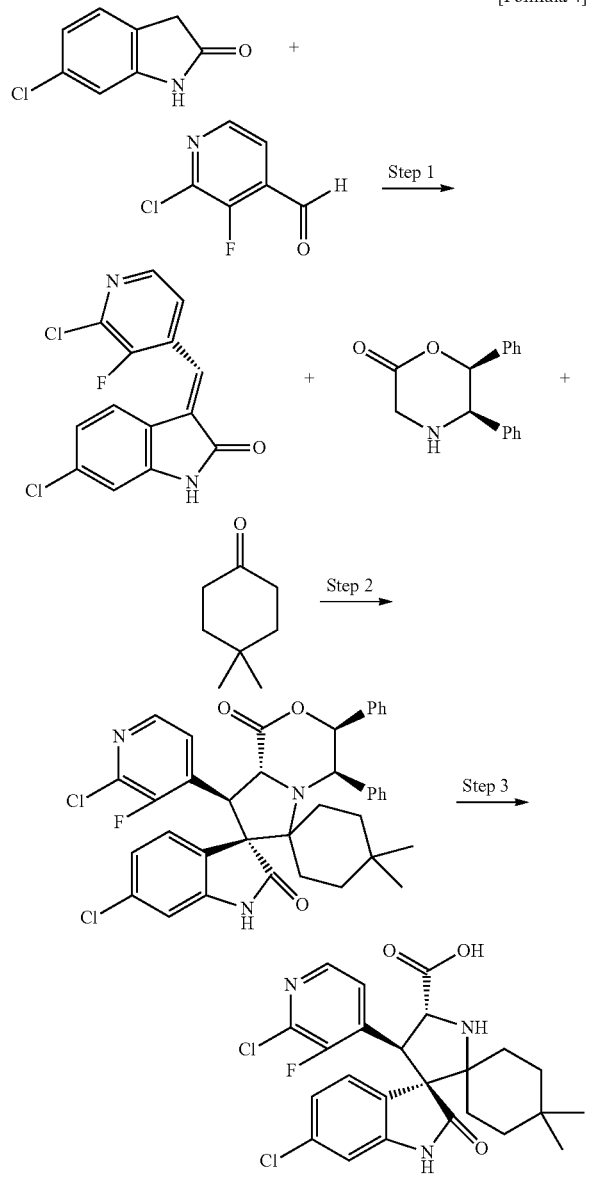

[Step 1] (3E/Z)-6-chloro-3-[(2-chloro-3-fluoropyridin-4-yl)methylene]-1,3-dihydro-2H-indol-2-one N,N-Diisopropylethylamine (0.46 ml, 2.63 mmol) was added to a methanol (130 ml) solution of 6-chloro-1,3-dihydro-2H-indol-2-one (2.20 g, 13.11 mmol) and 2-chloro-3-fluoroisonicotinaldehyde (2.20 g, 13.8 mmol) and the resulting mixture was heated to reflux for 16 hours. After cooling, the precipitate was collected by filtration, washed with cold methanol and dried to give 3.37 g (83%) of the title compound as a solid.

MS (APCI) m/z: 309 (M+H)$^+$.

[Step 2] (3'S, 4'R, 7'S,8'S,8a'R)-6''-chloro-8'-(2-chloro-3-fluoropyridin-4-yl)-4,4-dimethyl-3',4'-diphenyl-3',4',8',8a'-tetrahydro-1'H-dispiro[cyclohexane-1,6'-pyrrolo[2,1-c][1,4]oxazine-7',3''-indole]-1',2''(1''H)-dione A boron trifluoride-diethyl ether complex (0.15 ml, 1.20 mmol) and 4 A molecular sieves (powder) (3 g) were added to a tetrahydrofuran (30 ml) solution of the compound (1.86 g, 6.00 mmol) obtained in Step 1, (5R,6S)-5,6-diphenylmorpholin-2-one (1.67 g, 6.60 mmol), and 4,4-dimethylcyclohexanone (0.83 g, 6.60 mmol) under a nitrogen atmosphere and the resulting mixture was stirred under heating at 70° C. for 7 days. After cooling, insoluble matter was removed by filtration through celite and the filtrate was washed with brine and then dried over anhydrous sodium sulfate. The solvent was evaporated under reduced pressure and the residue was purified by silica gel column chromatography [n-hexane:ethyl acetate=4:1→1:1 (v/v)] to give 3.39 g (84%) of the title compound as a solid.

$^1$H-NMR (400 MHz, CDCl$_3$) δ: 0.21 (3H, s), 0.53 (3H, s), 0.89-1.08 (3H, m), 1.28-1.43 (3H, m), 1.73-1.81 (1H, m), 2.23-2.33 (1H, m), 4.58 (1H, d, J=11.0 Hz), 4.86 (1H, d, J=3.2 Hz), 5.31 (1H, d, J=11.0 Hz), 6.25 (1H, d, J=8.3 Hz), 6.67 (1H, dd, J=8.3, 1.8 Hz), 6.72-6.77 (2H, m), 6.93 (1H, d, J=1.8 Hz), 7.04-7.17 (6H, m), 7.18-7.25 (3H, m), 7.79 (1H, t, J=4.6 Hz), 7.99 (1H, s), 8.29 (1H, d, J=5.0 Hz).

MS (APCI) m/z: 670 (M+H)$^+$.

[Step 3] (4'S,5'R)-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxylic acid The compound (630 mg, 0.94 mmol) obtained in Step 2 was dissolved in acetonitrile (10 ml) and water (4 ml), potassium carbonate (130 mg, 0.94 mmol) was added and the resulting mixture was heated to reflux at 85° C. for 16 hours. After cooling, anhydrous magnesium sulfate (113 mg, 0.94 mmol) was added and the resulting mixture was stirred at room temperature for 15 minutes. After extraction with ethyl acetate, the organic layer was washed with brine and dried over anhydrous magnesium sulfate. The solvent was evaporated under reduced pressure to give (4'S,5'R)-6''-chloro-4'-(2-chloro-3-fluoropyridin-4-yl)-1'-[(1R,2S)-2-hydroxy-1,2-diphenylethyl]-4,4-dimethyl-2''-oxo-1'',2''-dihydrodispiro[cyclohexane-1,2'-pyrrolidine-3',3''-indole]-5'-carboxylic acid (650 mg, 100%) as a solid [MS (ESI) m/z: 688 (M+H)$^+$]. The carboxylic acid (650 mg, 0.94 mmol) obtained was dissolved in methanol (30 ml) and water (8 ml), cerium (IV) diammonium nitrate (1.55 g, 2.82 mmol) was added under ice cooling and the resulting mixture was stirred at the same temperature for 30 minutes. Potassium carbonate (780 mg, 5.64 mmol) was added under ice cooling and the resulting mixture was stirred at the same temperature for 1 hour. Insoluble matter was removed by filtration through celite, then the filtrate was concentrated under reduced pressure and water was added to the residue obtained, followed by extraction with ethyl acetate. The organic layer was washed with brine and dried over anhydrous sodium sulfate. The solvent was evaporated under reduced pressure and the residue obtained was purified by silica gel column chromatography [chloroform:methanol=20:1→4:1 (v/v)] to give 152 mg (33%) of the title compound as a solid.

$^1$H-NMR (500 MHz, CD$_3$OD) δ: 0.74 (3H, s), 0.9 (3H, s), 1.29-1.44 (2H, m), 1.48-1.58 (2H, m), 1.64-1.76 (1H, m), 1.94-2.02 (1H, m), 2.11 (1H, ddd, J=14.0, 14.0, 4.0 Hz), 2.43-2.53 (1H, m), 5.07 (1H, d, J=10.3 Hz), 5.32 (1H, d, J=10.3 Hz), 6.84 (1H, d, J=1.7 Hz), 7.16 (1H, dd, J=8.3, 2.0 Hz), 7.63 (1H, dd, J=8.0, 2.3 Hz), 7.75 (1H, t, J=5.2 Hz), 8.15 (1H, d, J=5.2 Hz).

MS (ESI) m/z: 492 (M+H)+.

Reference Example 2

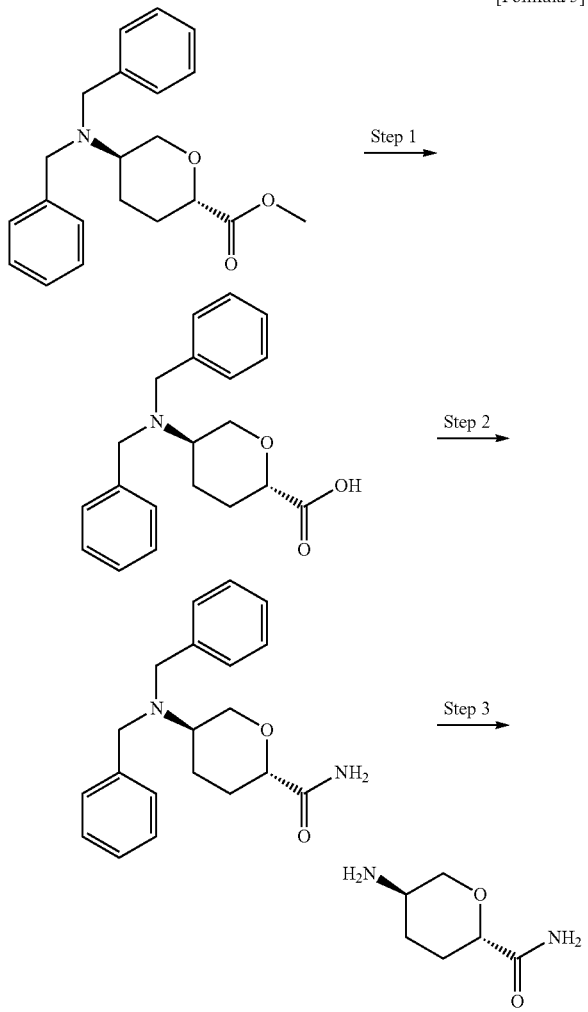

[Formula 5]

[Step 1] 2,6-anhydro-3,4,5-trideoxy-5-(dibenzylamino)-L-erythro-hexonic acid

Methyl 2,6-anhydro-3,4,5-trideoxy-5-(dibenzylamino)-L-erythro-hexonate Methyl 2,6-anhydro-3,4,5-trideoxy-5-(dibenzylamino)-L-erythro-hexonate (1.60 g, 4.70 mmol) was dissolved in methanol (30 ml), 1N sodium hydroxide solution (10 ml) was gradually added under ice cooling and then the resulting mixture was stirred at room temperature for 3 hours. Dowex 50W-X8 was added to the reaction mixture to adjust its pH to 5 to 6, insoluble matter was removed by filtration and then the filtrate was concentrated under reduced pressure to give 1.7 g (100%) of the title compound as a solid.

$^1$H-NMR (400 MHz, CDCl$_3$) δ: 1.18-1.26 (1H, m), 1.36-1.48 (1H, m), 1.79-1.97 (2H, m), 2.62 (1H, t, J=11.0 Hz), 3.18 (1H, t, J=10.4 Hz), 3.40 (1H, d, J=11.5 Hz), 3.51-3.61 (4H, m), 3.90-3.99 (1H, m), 7.12-7.38 (10H, m).

MS (ESI) m/z: 326 (M+H)+.

[Step 2] (2S,5R)-5-(dibenzylamino)tetrahydro-2H-pyran-2-carboxamide

The compound (870 mg, 2.67 mmol) obtained in Step 1 above was dissolved in N,N-dimethylformamide (30 ml), 1-hydroxybenzotriazole (361 mg, 2.67 mmol) and 1-ethyl-3-(3-dimethylaminopropyl)carbodiimide hydrochloride (614 mg, 3.20 mmol) were added and the resulting mixture was stirred at room temperature for 15 minutes. Ammonium chloride (285 mg, 5.44 mmol) and N,N-diisopropylethylamine (1.86 ml, 10.7 mmol) were added and the resulting mixture was stirred at room temperature for 8 hours. The reaction mixture was diluted with ethyl acetate and the organic layer was washed with saturated sodium bicarbonate solution and brine in this order and dried over anhydrous sodium sulfate. The solvent was evaporated under reduced pressure to give 495 mg (57%) of the title compound as a solid.

$^1$H-NMR (400 MHz, CDCl$_3$) δ: 1.35-1.45 (1H, m), 1.60-1.70 (1H, m), 2.10-2.18 (1H, m), 2.21-2.28 (1H, m), 2.76 (1H, tt, J=11.4, 4.0 Hz), 3.44 (1H, t, J=10.9 Hz), 3.67 (4H, q, J=14.2 Hz), 3.71-3.73 (1H, m), 4.04 (1H, dq, J=11.0, 2.1 Hz), 5.35 (1H, s), 6.40 (1H, s), 7.21-7.36 (10H, m).

MS (ESI) m/z: 325 (M+H)+.

[Step 3] (2S,5R)-5-aminotetrahydro-2H-pyran-2-carboxamide

The compound (490 mg, 1.51 mmol) obtained in Step 2 above was dissolved in ethanol (10 ml), 20% palladium hydroxide (100 mg) was added and the resulting mixture was stirred at room temperature for 16 hours under a hydrogen atmosphere. The catalyst was removed by filtration through celite, then the solvent in the filtrate was evaporated under reduced pressure and the residue was dried to give 215 mg (99%) of the title compound as a solid.

$^1$H-NMR (400 MHz, DMSO-d$_6$) δ: 1.11-1.22 (1H, m), 1.25-1.35 (1H, m), 1.83-1.91 (2H, m), 2.51-2.60 (1H, m), 2.90 (1H, t, J=10.5 Hz), 3.52 (1H, d, J=11.9 Hz), 3.78-3.84 (1H, m), 6.99 (1H, br s), 7.09 (1H, br s).

MS (ESI) m/z: 145 (M+H)+.

Test Example 1 Mdm2/p53 Binding Assay

A protein dilution containing 6.25 nM each of His-p53 (fusion protein of a p53 partial protein having p53 amino acids at positions 1 to 132, with a histidine protein) and GST-Mdm2 (fusion protein of a Mdm2 partial protein, having Mdm2 amino acids at positions 25 to 108 with leucine residue 33 substituted by glutamic acid, with glutathione transferase) proteins was prepared using a protein buffer solution (20 mM HEPES pH 7.4, 150 mM NaCl, 0.1% BSA). This protein dilution was added in an amount of 8 µL/well to a 384-well plate (384-well low volume NBC, Corning Inc., catalog No: 3676).

Next, a test compound was diluted with DMSO to produce protein buffer solution containing 10% dilution, and this buffer solution was added in an amount of 4 µL/well to the plate.

Subsequently, a solution containing an XL665-labeled anti-His antibody (HTRF monoclonal anti-6HIS antibody labeled with XL665 (catalog No: 61HISXLB), Schering/Cisbio Bioassays) and a europium (Eu)-labeled anti-GST antibody (HTRF monoclonal anti-GST antibody labeled with europium cryptate, Schering/Cisbio Bioassays, catalog No: 61GSTKLB) at concentrations of 2.5 µg/mL and 0.325 µg/mL, respectively, was prepared using an antibody diluting buffer solution (20 mM HEPES pH 7.4, 150 mM NaCl, 0.1% BSA, 0.5 M KF). These dilutions were added in an amount of 8 µL/well (total reaction solution volume: 20 µl/well). Then, the plate was left at 25° C. for 1 hour.

Time-resolved fluorescence at 620 and 665 nm was measured at an excitation wavelength of 320 nm using a plate reader (ARVOsx, PerkinElmer Co., Ltd. or PHERAstar, BMG LABTECH). Ratio (R) was calculated using the measured values (RFU 620 nm and RFU 665 nm) according to the following formula:

$$R=(RFU 665\ nm-BI-C\times RFU 620\ nm)/RFU 620\ nm$$

BI: measured value at 665 nm of reaction solution (only each buffer solution) nonsupplemented with each protein, the compound, and the antibodies $$C(\text{correction factor})=(A-BI)/D$$

A and D: each measured value at 665 nm and 620 nm of reaction solution supplemented with only Eu-labeled anti-GST antibody solution.

The R value calculated from the well supplemented with His-p53, GST-Mdm2, the test compound, and each antibody was defined as R (sample). The R value calculated from the well supplemented with His-p53, GST-Mdm2, and each antibody but without the test compound was defined as R (control). The R value calculated from the well supplemented with GST-Mdm2, the test compound, and each antibody but without His-p53 was defined as R (background). T/C was calculated from the formula shown below. An $IC_{50}$ value for Mdm2/p53 binding was calculated by sigmoid fitting. The results are shown in Table 1.

$$T/C=(R(\text{sample})-R(\text{background}))/(R(\text{control})-R(\text{background}))$$

The compound (1) exhibited an $IC_{50}$ value of 0.1 µM or lower.

Test Example 2 Cell Growth Inhibition Assay

A cell growth inhibition assay was conducted using human lung cancer-derived cell line NCI-H460 having wild-type p53.

NCI-H460 cells were suspended in a medium (RPMI1640 medium containing 10% fetal bovine serum) and the suspension was inoculated in an amount of 500 cells/150 µL/well to a 96-well multiwell plate. A test compound was dissolved in DMSO and this solution was diluted with medium to prepare a sample solution (DMSO concentration: 1% or lower). On the next day of inoculation, medium nonsupplemented with the test compound or the sample solution was added in an amount of 50 µL/well. The MTT assay was conducted immediately after the medium was added in an amount of 50 µL on the next day of cell inoculation, and after the sample solution or the medium was added to cells followed by culturing at 37° C. for 3 days in a 5% $CO_2$ atmosphere. The MTT assay was conducted as shown below.

A 5 mg/mL MTT (3-(4,5-dimethylthiazol-2-yl)-2,5-diphenyltetrazolium bromide, Sigma-Aldrich Co., M-2128) solution was prepared using a phosphate buffer solution (Dulbecco's Phosphate-buffered Saline). This MTT solution was added in an amount of 20 µL/well. Then, the plate was cultured at 37° C. for 4 hours in a 5% $CO_2$ atmosphere. The plate was centrifuged at 1200 rpm for 5 minutes and then the culture supernatant was removed by aspiration using a dispenser. DMSO was added in an amount of 150 µL/well to dissolve generated formazan. The plate was stirred using a plate mixer for uniform color development from each well. The absorbance of each well was measured under conditions of OD 540 nm and reference 660 nm using a plate reader (SpectraMax PLUS384, Molecular Devices, CA, USA).

The OD value measured on the day of adding the sample solution was defined as S. The OD value measured three days after addition of the sample solution was defined as T. The OD value measured three days after addition of the DMSO dilution was defined as C. T/C (%) was determined at each concentration according to the calculation formula shown below to prepare a dose response curve, from which 50% growth inhibition concentration ($GI_{50}$ value) was calculated.

$$T/C(\%)=(T-S)/(C-S)\times 100$$

The compound (1) exhibited a cell growth inhibiting effect of $GI_{50}$ (µM)<0.1.

Preparation Example 1 <Capsule>

5 g of a crystal obtained in the Examples, 115 g of lactose, 58 g of corn starch, and 2 g of magnesium stearate can be mixed using a V-mixer and then filled in an amount of 180 mg/shell into No. 3 capsule shells to give capsules.

Preparation Example 2 <Tablet>

5 g of a crystal obtained in the Examples, 90 g of lactose, 34 g of corn starch, 20 g of crystalline cellulose, and 1 g of magnesium stearate can be mixed using a V-mixer and then compressed in a tableting machine in a mass of 150 mg/tablet to give tablets.

Preparation Example 3 <Suspension>

Methylcellulose is dispersed and dissolved in purified water to prepare a dispersion medium. A crystal obtained in the Examples is weighed into a mortar. The dispersion medium is added in small portions to the crystal while the mixture is well kneaded. Purified water is added to prepare 100 g of suspension.

The invention claimed is:
1. A crystal of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide represented by the following formula (1):

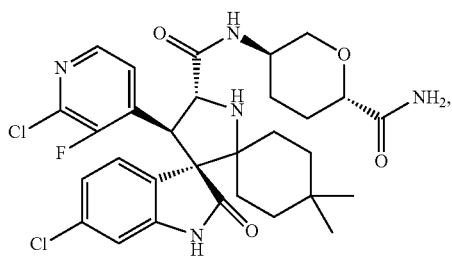 [SMILES: CC1(C)CCC2(CC1)N[C@@H](C(=O)N[C@@H]1CC[C@@H](C(N)=O)OC1)[C@H](c1ccnc(Cl)c1F)[C@]21C(=O)Nc2cc(Cl)ccc21]

wherein:

the crystal has the X-ray diffraction pattern as shown in FIG. 2 as determined by X-ray powder diffraction obtained by copper Kα radiation (wavelength λ=1.54 angstroms).

2. The crystal of claim 1, having characteristic peaks at diffraction angles 2θ of 7.62, 13.06, 15.10, 17.22, and 21.98 in an X-ray powder diffraction pattern obtained by copper Kα radiation (wavelength λ=1.54 angstroms).

3. A pharmaceutical composition comprising the crystal of claim 1 and a pharmaceutically acceptable carrier.

* * * * *